US006204003B1

(12) United States Patent
Steele et al.

(10) Patent No.: US 6,204,003 B1
(45) Date of Patent: Mar. 20, 2001

(54) METHODS FOR THE DIAGNOSIS OF FELINE INFECTIOUS ANEMIA

(75) Inventors: J. Kevin Steele, San Diego; David L. Telford, Carlsbad; John A. Cutting, San Diego, all of CA (US)

(73) Assignee: Synbiotics Corporation, San Diego, CA (US)

( * ) Notice: Subject to any disclaimer, the term of this patent is extended or adjusted under 35 U.S.C. 154(b) by 0 days.

(21) Appl. No.: 09/157,210

(22) Filed: Sep. 18, 1998

Related U.S. Application Data

(60) Provisional application No. 60/059,551, filed on Sep. 19, 1997.

(51) Int. Cl.[7] .................................................. G01N 33/554
(52) U.S. Cl. .................. 435/7.32; 424/184.1; 424/190.1; 424/264; 424/1; 435/7.1; 435/7.2; 435/243; 435/245; 435/252.1; 435/340; 435/351; 436/501; 436/512; 530/388.4

(58) Field of Search ............................. 424/184.1, 190.1, 424/264.1; 435/7.1, 7.2, 7.32, 245, 252.1, 243, 340, 351, 822, 863; 436/501, 512, 513, 518, 519, 520; 530/300, 350, 388.4

(56) References Cited

U.S. PATENT DOCUMENTS 5,350,672 9/1994 Oberst et al. .
5,399,485 3/1995 Regnery et al. .
5,621,076 * 4/1997 Kodama et al. ..................... 530/350

FOREIGN PATENT DOCUMENTS 940135330 11/1994 (CA) .
WO 96134884 4/1996 (WO) .
96/34884 * 11/1996 (WO) .

OTHER PUBLICATIONS

Sundquist et al. Protective immunity induced in chicken by a single immunization with *Mycoplasma gallisepticum* immunostimulating complexes. Vaccine vol. 14, No. 9 (1996) pp. 892–897.*

Abdelmoumen et al. Antigenic relatedness between seven avian Mycoplasma species as revealed by western blot analysis. Avian Diseases. vol. 39 (1995) pp. 250–262.*

Baseggio, et al. (1996) Size And Genomic Location Of The pMGA Multigene Family Of *Mycoplasma Gallisepticum*: Vetinary Record: V. 142, 1429–1435.

Bobade, P.A., et al. (1988) Feline haemobartonellosis: Clinical, haematological and pathological studies in natural infections and the relationship to infection with feline leukaemia virus, Vetinary Record: V. 122, 32–36.

Brown, L.A. (1986) Cambridge Intake, Vetinary Record: Nov. 22, 1996, 534.

Carney, et al. (1993) Feline Hemobartonellosis, Feline Infectious Diseases:V. 23 No. 1: 79–90.

Cotter, Susan, et al. (1975) Association of Feline Leukemia Virus with Lymphosarcoma and Other Disorders in the Cat, J AVMA: V. 166, No. 5: 449–454.

Fredricks, David, et al. (1996) Sequence–Based Identification of Microbial Pathogens: a Reconsideration of Koch's Postulates, Clinical Microbiology Reviews: V. 9, No. 1: 18–33.

Glew, Michelle, et al. (1995) Expression Studies On Four Members Of The pMGA Multigene Family in *Mycoplasma Gallisepticum* S6, Microbiology: V. 141 No. 3005–3014.

Greene, Craig (1984) Clinical Microbiology and Infectious Diseases of the Dog and Cat, College of Vetinary Medicine, Univ. of Georgia: Ch. 34, 576–587.

Grindem, C.B., et al. (1990) Risk Factors For Haemobartonella Felis Infection Cats, JAVMA: V. 196, No. 1:96–99.

Hayes, et al. (1973) Feline Infectious Anaemia. Risk By Age, Sex And Breed; Prior Disease; Seasonal Occurrence; Mortality, National Cancer Institute: V. 14:797–804.

Markham, P.F., et al. (1991) Characterization Of A Major Hemagglutinin Protein From *Mycoplasma Gallisepticum*, Infection an Immunity: V. 60, No. 9:3885–3891.

Markham, P.F., et al. (1991) Molecular Cloning of a Member of the Gene Family That Encodes pMGA, a Hemagglutinin of *Mycoplasma Gallisepticum*, Infection and Immunity: vol. 61, No. 3:903–909.

Markham, P.F., et al. (1994) The organisation of the multigene family which encodes the major cell surface protein, pMGA, or *Mycoplasma Gallisepticum*, FEBS: Letters 352: 347–352.

Nash, A.S., et al. (1986) Haemobartonella felis infection in cats from the Glasgow area, The Vetinary Record: vol. 119:373–375.

Rikihisa, Yasuko, et al. (1997) Western Immunoblot Analysis of *Haemobartonella Muris* And Comparison Of 16S rRNA Gene Sequences Of *H. muris, H. felis* and *Eperythrozoon suis*, Journal Of Clinical Microbiology: vol. 35, No. 4: 823–829.

Small, Erwin, et al. (1967) Morphologic Features of *Haemobartonella felis*, Am. J. Vet. Res., vol. 28, No. 124: 845–851.

Sutton, R.H. (1980) The Value Of A Single Haematological Examination In The Diagnosis Of Disease In The Cat: J. Small Anim. Pract: vol. 21: 339–345.

Genbank, Accession No. U88563, dated May 2, 1997.
Genbank, Accession No. U82963, dated Apr. 26, 1997.

(List continued on next page.)

*Primary Examiner*—Jeffrey Stucker
*Assistant Examiner*—Ulrike Winkler
(74) *Attorney, Agent, or Firm*—Knobbe Martens Olson & Bear, LLP

(57) ABSTRACT

The claimed invention is a method for determining whether a mammal is infected with *Haemobartonella felis* or for inducing an immune response against *Haemobartonella felis* using a polypeptide expressed by Mycoplasma. Preferably, the polypeptide is expressed by *Mycoplasma gallisepticum*. In a preferred embodiment the polypeptide is the pMGA protein expressed by the strain of *Mycoplasma gallisepticum* having ATCC deposit number 19610.

5 Claims, 9 Drawing Sheets-

OTHER PUBLICATIONS

Genbank, Accession No. U88564, dated May 2, 1997.
Genbank, Accession No. U88565, dated May 2, 1997.
Genbank, Accession No. U95297, dated Jun. 27, 1997.
Genbank, Accession No. L24488, dated Sep. 24, 1993.
Brown, D.R. et al., Taxonomy of the Feline Mycoplasmas *Mycoplasma felifaucium, Mycoplasma felimiutum, Mycoplasma feils, Mycoplasma gateae, Mycoplasma leocaptitvus, Mycoplasma leopharyngis, and Mycoplasma simbae* by 16S rRNA Gene Sequence Comparisons†, International Journal of Systematic Bacteriology, Jul. 1995, p. 560–564.
Krier, Julius P. et al., Section 9. Rickettsias and Chlamydias; Genus III. Haemobartonella Tyzzer and Weinman, 1939, p. 143.

Aman, Rudolf I. et al., Phylogenetic Identification and in Situ Detection of Individual Microbial Cells without Cultivation; Microbiological Reviews, Mar. 1995, p. 143–169.

Messick, Joanne B. et al., Development and Evaluation of a PCR–Based Array for Detection of *Haemobartonella feils* from Related Bacteria by Restriction Fragment Length Polymorphism Analysis; Journal of Clinical Microbiology, Feb. 1998, p. 462–466.

Berent, DVM, Linda M. et al., Detection of *Haemobartonella felis* in cats with experimentally induced acute and chronic infections, using a polymerase chain reaction assay; AJVR, vol. 59, No. 10, Oct. 1998, p. 615–620.

* cited by examiner

```
...16s→    10         20         30         40         50         60
            *          *          *          *          *          *
AAGCTTCATCCATGATTTAGCTTTTAAAGCCTTCGGGCGCTGAGGGATTGGGATATGCTC
TTCGAAGTAGGTACTAAATCGAAAATTTCGGAAGCCCGCGACTCCCTAACCCTATACGAG 70         80         90        100        110        120
            *          *          *          *          *          *
TATTAGCTAGTTGGCGGGATAAAAGCCCACCAAGGCAATGATAGATTGCTGGTCTTAGAG
ATAATCGATCAACCGCCCTATTTTCGGGTGGTTCCGTTACTATCTAACGACCAGAATCTC 130        140        150        160        170        180
            *          *          *          *          *          *
GATGAACAGCCACAATGGGATTGAGATACGGCCCATATTCNTACGGGAAGCAGCAGTAGG
CTACTTGTCGGTGTTACCCTAACTCTATGCCGGGTATAAGNATGCCCTTCGTCGTCATCC 190        200        210        220        230        240
            *          *          *          *          *          *
GAATCTTCCACAATGGACGAAAGTCTGATGGAGCAATACCATGTGAACGATGAAGGCCTT
CTTAGAAGGTGTTACCTGCTTTCAGACTACCTCGTTATGGTACACTTGCTACTTCCGGAA 250        260        270        280        290        300
            *          *          *          *          *          *
TTTGGTTGTAAAGTTCTTTTACGAGGGATAATTATGATAGTACTTCGTGAATAAGTGACA
AAACCAACATTTCAAGAAAATGCTCCCTATTAATACTATCATGAAGCACTTATTCACTGT 310        320        330        340        350        360
            *          *          *          *          *          *
GCAAACTATGTGCCAGCAGCTGCGGTAATACATAGGTCGCGAGCATTATTCGGATTTATT
CGTTTGATACACGGTCGTCGACGCCATTATGTATCCAGCGCTCGTAATAAGCCTAAATAA 370        380        390        400        410        420
            *          *          *          *          *          *
GGGCGTAAAGCAAGCGCAGGCGGATGTGTAAGTTCTGTGTTAAATGCAGCTACTCAATAG
CCCGCATTTCGTTCGCGTCCGCCTACACATTCAAGACACAATTTACGTCGATGAGTTATC
```

FIG. 1B

```
                430         440         450         460         470         480
                 *           *           *           *           *           *
       TTGTATGCACCGAATACTACATGTCTAGATTGTGGTAGGGAGTTTCGGAATTAAGCATGG
       AACATACGTGGCTTATGATGTACAGATCTAACACCATCCCTCAAAGCCTTAATTCGTACC 490         500         510         520         530         540
                 *           *           *           *           *           *
       AGCGGTGGAATGTGTAGATATGCTTAAGAACACCAGAGGCGCCGGCGGAAACTTAGGCCA
       TCGCCACCTTACACATCTATACGAATTCTTGTGGTCTCCGCGGCCGCCTTTGAATCCGGT 550         560         570    FIA-12→ 580         590         600
                 *           *           *           *           *           *
       TAAATGACGCTTAGGCTTGAAAGTGTGRGGAG[CAAATGGGATTAGRTACCCC]AGTAGTYC
       ATTTACTGCGAATCCGAACTTTCACACYCCTCGTTTACCCTAATCYATGGGGTCATCARG 610         620         630         640   FIA-14→ 650         660
                 *           *           *           *           *           *
       ACACCGTAAACGATGGGTATTAGATATTAGGGCTKTAG[CTTTAGTGTTGTAGCTTACGC]G
       TGTGGCATTTGCTACCCATAATCTATAATCCCGAMATCGAAATCACAACATCGAATGCGC 670         680         690         700         710         720
                 *           *           *           *           *           *
       TTAAATACCCCGCCTGGGTAGTACATATGCAAATATGAAACTCAAAGGAATTGACGGGGA
       AATTTATGGGGCGGACCCATCATGTATACGTTTATACTTTGAGTTTCCTTAACTGCCCCT 730         740         750         760         770         780
                 *           *           *           *           *           *
       CCTGAACAAGTGGTGGAGCATGTTGCTTAATTCGATAATACACGAAAAACCTTACCAAGG
       GGACTTGTTCACCACCTCGTACAACGAATTAAGCTATTATGTGCTTTTTGGAATGGTTCC 790         800         810         820         830         840
                 *           *           *           *           *           *
       TTTGACATCCCTCGCAAAGCTATAGAAATATAGTAGAGGTTATCGAGGTGACAGGTGGTG
       AAACTGTAGGGAGCGTTTCGATATCTTTATAT[CATCTCCAATAGCTCCACTG]TCCACCAC
                                                    ←FIA-13
                850         860         870         880         890         900
                 *           *           *           *           *           *
       CATGGCTGTCGTCAGCTCGTGTCTTGAGATGTTTGGTTAAGTCCCGCAACGAGCGCAACC
       GTACCGACAGCAGTCGAGCACAGAACTCTACAAACCAATTCAGGGCGTTGCTCGCGTTGG 910         920         930         940         950         960
                 *           *           *           *           *           *
       CCACTCTTTAGTTACTTGTCTAAAGAGRCTGCACAGTAATGTAGAGGAAGGATGGGATCA
       GGT[GAGAAATCAATGAACAGATTTCTC]YGACGTGTCATTACATCTCCTTCCTACC[CTAGT
                ←FIA-11
                970         980         990        1000        1010        1020
                 *           *           *           *           *           *
       CGTCAAGTCATCATGCCCCTTATGCCTTGGGCTGCAAACGTGCTACAATGGCGAACACAA
       GCAGTTCAGTAGTAC]GGGGAATACGGAACCCGACGTTTGCACGATGTTACCGCTTGTGTT
       ←16s.02T
```

FIG. 1C

```
         1030      1040      1050      1060      1070      1080
           *         *         *         *         *         *
TGTGTTGCAGACCAGCGATGGTAAGCTAATCACCAAATTTCGTCTCAGTTCGGATAGGAG
ACACAACGTCTGGTCGCTACCATTCGATTAGTGGTTTAAAGCAGAGTCAAGCCTATCCTC 1090      1100      1110      1120      1130      1140
           *         *         *         *         *         *
GCTGCAATTCGCCTCCTTGAAGTTCCAATCACTAGTAATCCCGTGTCAGCTATATCGGGG
CGACGTTAAGCGGAGGAACTTCAAGGTTAGTGATCATTAGGGCACAGTCGATATAGCCCC 1150      1160      1170      1180      1190      1200
           *         *         *         *         *         *
TGAATCCGTTCCCAGGTCTTGTACACACCGCCCGTCAAACTATGAGACCAGTGGGCATTT
ACTTAGGCAAGGGTCCAGAACATGTGTGGCGGGCAGTTTGATACTCTGGTCACCCGTAAA
                                                    ←—16s—┐
         1210      1220      1230      1240      1250      1260
           *         *         *         *         *         *
AAAAATACATTCATTTGTATCTAGAGTGAACATTCTGATTGGAGTTAAGTCGTAACAAGG
TTTTTATGTAAGTAAACATAGATCTCACTTGTAAGACTAACCTCAATTCAGCATTGTTCC
                                               approximate end of 16s ⇧
         1270      1280      1290      1300      1310      1320
           *         *         *         *         *         *
TACCCGTACGAGAACGTGCGGGTGGATAATCTTCAAGTTATGAGATGATAGAGCCTTTTT
ATGGGCATGCTCTTGCACGCCCACCTATTAGAAGTTCAATACTCTACTATCTCGGAAAAA 1330      1340      1350      1360      1370      1380
           *         *         *         *         *         *
GGGCTTTATTTAGTAGAGGTTGTAACTAGAATAAATTCAAGTCGTATAGATAGATTTGAA
CCCGAAATAAATCATCTCCAACATTGATCTTATTTAAGTTCAGCATATCTATCTAAACTT 1390      1400      1410      1420      1430      1440
           *         *         *         *         *         *
AACTTCTAGGCGGATGATTCTCAGTTTTGAGAAAGCTAGAACTTTCTCAGTTTGCTTTTG
TTGAAGATCCGCCTACTAAGAGTCAAAACTCTTTCGATCTTGAAAGAGTCAAACGAAAAC
                                        ─→ approximate beginning of 23s
         1450      1460      1470      1480      1490      1500
           *         *         *         *         *         *
AAAGGAAAAGATAATAACCGAGTTAACTTAGATNGTTNATCATACGTAAATTATTAAGAG
TTTCCTTTTCTATTATTGGCTCAATTGAATCTANCAANTAGTATGCATTTAATAATTCTC
                                        ↳→
         1510      1520      1530      1540      1550      1560
           *         *         *         *         *         *
CTAAAGGTGGATTTCTTGGAAATGGTAGACTATGAAGGACGTGCCAATCTGCGATAAGCT
GATTTCCACCTAAAGAACCTTTACCATCTGATACTTCCTGCACGGTTAGACGCTATTCGA 1570      1580      1590      1600      1610      1620
           *         *         *         *         *         *
AGGGGTAGCCGATNAGGGGCTTTAATCCCTAGATCTCCGAATGTAGAAATACAACATTTT
TCCCCATCGGCTANTCCCCGAAATTAGGGATCTAGAGGCTTACATCTTTATGTTGTAAAA
```

FIG. 1D

```
          1630       1640       1650       1660       1670       1680
            *          *          *          *          *          *
GAAAGATTTGTTACTTGTCGGCCAATTCATAACCGACAAGGGTGAACTTCGTGAAGTGAA
CTTTCTAAACAATGAACAGCCGGTTAAGTATTGGCTGTTCCCACTTGAAGCACTTCACTT
          1690       1700       1710       1720       1730       1740
            *          *          *          *          *          *
ACATCTCAGTNGCGAAAGGAAAAGAAAGAGAATTCGATTCCCTCAGTAGTGGTGAGCGAA
TGTAGAGTCANCGCTTTCCTTTTCTTTCTCTTAAGCTAAGGGAGTCATCACCACTCGCTT
          1750       1760       1770       1780       1790       1800
            *          *          *          *          *          *
AGGGGAACAGGCCAAACCGGTTTTACCGGGGTTGTAGGACATTTATATGGAATCAGAAGT
TCCCCTTGTCCGGTTTGGCCAAAATGGCCCCAACATCCTGTAAATATACCTTAGTCTTCA
          1810       1820       1830       1840       1850       1860
            *          *          *          *          *          *
ATAGGAGAAGTCTTTGGAAAGAGACGGCATAGAGGGCGATCCCCCCGTATCCGACATGCT
TATCCTCTTCAGAAACCTTTCTCTGCCGTATCTCCCGCTAGGGGGGCATAGGCTGTACGA
          1870       1880       1890       1900       1910       1920
            *          *          *          *          *          *
TCTGATTACTGAGTGCATCCTGAGTAGGGCGGGACACGTGTAATCCTGTCTGAATCTGCC
AGACTAATGACTCACGTAGGACTCATCCCGCCCTGTGCACATTAGGACAGACTTAGACGG
          1930       1940       1950       1960       1970       1980
            *          *          *          *          *          *
CAGACCATTGGGTAAGCCTAAATACTAACCATTTACCGATAGTGAACAAGTACTGTGAAG
GTCTGGTAACCCATTCGGATTTATGATTGGTAAATGGCTATCACTTGTTCATGACACTTC
          1990       2000       2010       2020       2030       2040
            *          *          *          *          *          *
GAAAGATGAAAAGAACCCAGAGATGGGAGTGAAATAGATCATGAAACCTATAGCTTACGA
CTTTCTACTTTTCTTGGGTCTCTACCCTCACTTTATCTAGTACTTTGGATATCGAATGCT
          2050       2060       2070       2080       2090       2100
            *          *          *          *          *          *
AGAGTCATAGGCCATTTATGGCTAATGGCGTGCGTTTTGAAGTATGAGCCGGCGAGTTAT
TCTCAGTATCCGGTAAATACCGATTACCGCACGCAAAACTTCATACTCGGCCGCTCAATA
          2110       2120       2130       2140       2150       2160
            *          *          *          *          *          *
TGTTGCATGCAAGGTTAAGCAATCAAAAGCGGAGCCGTATCGAAAGCGAGTGTGAATAGT
ACAACGTACGTTCCAATTCGTTAGTTTTCGCCTCGGCATAGCTTTCGCTCACACTTATCA
          2170       2180       2190       2200       2210       2220
            *          *          *          *          *          *
GCGTTTAGTATGTGGCAATAGACCCGAAACGGGATGATCTATCCATGGGCAGGTTGAAGG
CGCAAATCATACACCGTTATCTGGGCTTTGCCCTACTAGATAGGTACCCGTCCAACTTCC
          2230       2240       2250       2260       2270       2280
            *          *          *          *          *          *
TGGAGTAATATCCATTGGAGGACCGAACCGACTACCGTTGAAATGTTAGCGGATGACTTG
ACCTCATTATAGGTAACCTCCTGGCTTGGCTGATGGCAACTTTACAATCGCCTACTGAAC
```

FIG. 1E

```
         2290       2300       2310       2320       2330       2340
           *          *          *          *          *          *
TGGATAGGGGTGAAATTCCAATCGAATTCCGTGATAGCTGGTTCTCGTCGAAATAGTTTT
ACCTATCCCCACTTTAAGGTTAGCTTAAGGCACTATCGACCAAGAGCAGCTTTATCAAAA 2350       2360       2370       2380       2390       2400
           *          *          *          *          *          *
AGGACTAGCGTTGGATTATCCGATGCTTTGGAGGTAAAGCACTGAATTCATGATGGCGCA
TCCTGATCGCAACCTAATAGGCTACGAAACCTCCATTTCGTGACTTAAGTACTACCGCGT 2410       2420       2430       2440       2450       2460
           *          *          *          *          *          *
ATCTTTGTGTACTGAATGAAATTAAACTTTGAATGCCAAAGTGTCTACTCCAGCAGTGAG
TAGAAACACATGACTTACTTTAATTTGAAACTTACGGTTTCACAGATGAGGTCGTCACTC 2470       2480       2490       2500       2510       2520
           *          *          *          *          *          *
ACTATGGGGATAAGCTCCATGGTCATGAGGGAAAGAGCCCAGACTAACAAATAAGGTCC
TGATACCCCCTATTCGAGGTACCAGTACTCCCTTTCTCGGGTCTGATTGTTTATTCCAGG 2530       2540       2550       2560       2570       2580
           *          *          *          *          *          *
CTAAATTTGGCTAAGTGGAGAAGGAAGTCGAAATTCTTAAACAACTAGTATGTTGGCTTA
GATTTAAACCGATTCACCTCTTCCTTCAGCTTTAAGAATTTGTTGATCATACAACCGAAT 2590       2600       2610       2620       2630       2640
           *          *          *          *          *          *
GAAGCAGCCACCATTTAAAGAGTGCGTAACAGCTCACTAGTCTAGTTTTTCGGCACCGAA
CTTCGTCGGTGGTAAATTTCTCACGCATTGTCGAGTGATCAGATCAAAAAGCCGTGGCTT 2650       2660       2670       2680       2690       2700
           *          *          *          *          *          *
GGTATAACGGGGCTAAGCCAAATACCGAATTTTTAGACTATTTATATAGTGGTAGACGAG
CCATATTGCCCCGATTCGGTTTATGGCTTAAAAATCTGATAAATATATCACCATCTGCTC 2710       2720       2730       2740       2750       2760
           *          *          *          *          *          *
TGTTGTATTAGCGCGAAGGCTGAGCGTGAGCACAGTTGGAGTTAATACAAGTAAGGATGC
ACAACATAATCGCGCTTCCGACTCGCACTCGTGTCAACCTCAATTATGTTCATTCCTACG 2770       2780       2790       2800       2810       2820
           *          *          *          *          *          *
CGGCGTGAGTAACGTATGAAAGTTAAAATCTTTCTAGCCGATTGATCAAGGTTTCCAGGG
GCCGCACTCATTGCATACTTTCAATTTTAGAAAGATCGGCTAACTAGTTCCAAAGGTCCC 2830       2840       2850       2860       2870       2880
           *          *          *          *          *          *
CAAGGGTCATCCTCCCTGGGTTAGTCGGTCCTAAGATGAGGCCGAGAGGCGTAGTCGATG
GTTCCCAGTAGGAGGGACCCAATCAGCCAGGATTCTACTCCGGCTCTCCGCATCAGCTAC 2890       2900       2910       2920       2930       2940
           *          *          *          *          *          *
GGCAGCGAGTTAATATTCTTGCACCAGTTTAGCTAGTGATGGGTTGACAGAAGAGGTTAA
CCGTCGCTCAATTATAAGAACGTGGTCAAATCGATCACTACCCAACTGTCTTCTCCAATT
```

FIG. 1F

```
          2950       2960       2970       2980       2990       3000
            *          *          *          *          *          *
TGCGGGCGGGTTACTGGATTCCCGCTTAAGCTGCAAGTGTTTNGGGTAGTAAAATACGCC
ACGCCCGCCCAATGACCTAAGGGCGAATTCGACGTTCACAAANCCCATCATTTTATGCGG 3010       3020       3030       3040       3050       3060
            *          *          *          *          *          *
CGATTTAAGCGTGAGCAGTGAATACGAGCGAACCCTTCGGGTAGTAGTGAAGTCGCAAAC
GCTAAATTCGCACTCGTCACTTATGCTCGCTTGGGAAGCCCATCATCACTTCAGCGTTTG 3070       3080       3090       3100       3110       3120
            *          *          *          *          *          *
ATCATATTCTCAAGAAAAGACTCTAAACTTATGGCTAATCTGTCCGTACCTAGAACGAAC
TAGTATAAGAGTTCTTTTCTGAGATTTGAATACCGATTAGACAGGCATGGATCTTGCTTG 3130       3140       3150       3160       3170       3180
            *          *          *          *          *          *
ACANGTGATCAGGGAGAATATCCCAAGGCTATCGAGATAACTATAGTTAAGGAACTCTGC
TGTNCACTAGTCCCTCTTATAGGGTTCCGATAGCTCTATTGATATCAATTCCTTGAGACG 3190       3200       3210       3220       3230       3240
            *          *          *          *          *          *
AAAATAGCCCCGTAACTTCGGGAGAAGGGTGCCTAATTTGCNTTAGGCCACAGTAAAGAA
TTTTATCGGGGCATTGAAGCCCTCTTCCCACGGATTAAACGNAATCCGGTGTCATTTCTT 3250       3260       3270       3280       3290       3300
            *          *          *          *          *          *
TGAGGGGGGACTGTTTAACAAAAACATAGCTTTATGCGAAATCGTAAGANNAGGTATATG
ACTCCCCCCTGACAAATTGTTTTTGTATCGAAATACGCTTTAGCATTCTNNTCCATATAC 3310       3320       3330       3340       3350       3360
            *          *          *          *          *          *
AGGNGANACCTGCCCAGTGCCAGAAGGTCAATGAAGGATGTTAGCTTTTGCGAAGCATTT
TCCNCTNTGGACGGGTCACGGTCTTCCAGTTACTTCCTACAATCGAAAACGCTTCGTAAA 3370       3380       3390       3400       3410       3420
            *          *          *          *          *          *
AACTTAAGCCCTGGTGAACGGCGGCCGTAACTATAACGGTCCTAAGGTAGCGAAATTCCT
TTGAATTCGGGACCACTTGCCGCCGGCATTGATATTGCCAGGATTCCATCGCTTTAAGGA 3430       3440       3450       3460       3470       3480
            *          *          *          *          *          *
AACTTAAGCCCTGGTGAACGGCGGCCGTAACTATAACGGTCCTAAGGTAGCGAAATTCCT
TTGAATTCGGGACCACTTGCCGCCGGCATTGATATTGCCAGGATTCCATCGCTTTAAGGA 3490       3500       3510       3520       3530       3540
            *          *          *          *          *          *
GGCTCGGTGAAATCCTGGTGAGAGTGAAGACACTCTCTTGCCGCTATGGGACGGAAAGAC
CCGAGCCACTTTAGGACCACTCTCACTTCTGTGAGAGAACGGCGATACCCTGCCTTTCTG

3550
            *
CCTATGAAGCTT
GGATACTTCGAA
```

```
            10                  20                  30                  40                  50                  60                  70
             *                   *                   *                   *                   *                   *                   *
TT GAT ATT GTG ATG GGA GAA TAT CAG AAT ATT CAA GAT AGT AAC CCA GTA TTC TTC TTC CCA GCA CTA TCC CAA
   D   I   V   M   G   E   Y   Q   N   I   Q   D   S   N   P   V   F   F   F   P   A   L   S   Q>
AA CTA TAA CAC TAC CCT CTT ATA GTC TTA TAA GTT CTA TCA CTT CAT AAG GGT CGT GAT AGG GTT
            80                  90                 100                 110                 120                 130                 140
             *                   *                   *                   *                   *                   *                   *
TAT TGA CTA CTT AAA AGA AGC CTA ATT CAG CAG TAT GAA AAG GTT TTG AAT ATC TAT GAT GAC AAC TAC
ATA ACT GAT GAA TTT TCT TCG ATA GTC GTC TAA CTT CAA AAC TTA TAG ATA TAT CTA CTG TTG ATG
 Y   *   L   L   K   R   S   L   I   Q   Q   Y   E   K   V   L   N   I   Y   L   D   D   N   Y>
           150                 160                 170                 180                 190                 200                 210                 220
            *                   *                   *                   *                   *                   *                   *                   *
GAG ATA TTT GAA GAT GAG ATT AGA CAA GCT AAG GTA TCT TTG AAT AAT TTA ATC TGG AAG
CTG TAT AAA CTT CTA CTC TAA TCT GTT CGA TTC CAT AGA AAT NTT AGA AAT NAA TTA AAT TAG ACC TTC
 E   I   F   E   D   E   I   R   Q   A   K   V   X   R   N   K   V   S   L   N   L   I   W   K>
           230                 240                 250                 260                 270                 280                 290
            *                   *                   *                   *                   *                   *                   *
CTT CAG AAA ATA GAT CCT GAA TTT AAT GAG TCA CAG AAG AAT CTT CTC TTC CTA AAG GAT ATG
GAA GTC TTT TAT CTA GGA CTT AAA TTA CTC AGT GTC TTC TTA GAA GAG AAG GAT TTC CTA TAC
 L   Q   K   I   D   P   E   F   N   E   S   Q   K   Y   M   Q   S   Q   K   N   L   L   F   L   K   D   M>

FIG. 2A

| FIG. 2A |
| FIG. 2B |
| FIG. 2C |

```
300         310         320         330         340         350         360         370
 *           *           *           *           *           *           *           *
AAG GGA AGT GTG GAA CCT GGA GGT TCT GAG ATT CCA GAT GAT TTA GGG GAA CTG GAG TGT TGA GGA AGG ATT
TTC CCT TCA CAC CTT GGA CCT CCA AGA CTC TAA GGT CTA CTA AAT CCC CTT GAC CTC ACA ACT CCT TCC TAA
 K   G   S   V   E   P   G   G   S   E   I   P   D   D   L   G   E   L   E   C   *   G   R   I>

380         390         400         410         420         430         440
 *           *           *           *           *           *           *
GAA AAA CTT GAA ACA GTT TAT TAC AGA GAA CGC TTT CCT TAA GAA GTG AGA GCC GGA AAT AAT AAG ATC AGG
CTT TTT GAA CTT TGT CAA ATA ATG TCT CTT GCG AAA GGA ATT CTT CAC TCT CGG CCT TTA TTA TTC TAG TCC
 E   K   L   E   T   V   Y   Y   R   E   R   F   P   *   E   V   R   A   G   N   N   K   I   R>

450         460         470         480         490         500         510         520
 *           *           *           *           *           *           *           *
AAC TTG GAG CTC TAC CTC GAG GCC AAG TTG ACT TAC ATA AGA CAG AAG TTC ATG GGA CTT CAA GTT CAA ATT
TTG AAC CTC GAG ATG GAG CTC CGG TTC AAC TGA ATG TAT TCT GTC TTC AAG TAC CCT GAA GTT CAA GTT TAA
 N   L   E   L   Y   L   E   A   K   L   T   Y   I   R   Q   K   F   M   G   L   Q   V   Q   I>

530         540         550         560         570         580         590
 *           *           *           *           *           *           *
AGA CAT GAT GAC AGT GAG GAT AAG AAC CTT TTG AGA TTA ACT TCC CTT CAT GAT GCT TGG ACT TCC CTA TTT GAG AAG
TCT GTA CTA CTG TCA CTC CTA TTC TTG GAA AAC TCT AAT TGA AGG GAA GTA CTA CGA ACC TGA AGG GAT AAA CTC TTC
 R   H   D   D   S   E   D   K   N   L   L   R   L   T   S   L   H   D   A   W   T   S   L   F   E   K>

600         610         620         630         640         650         660         670
 *           *           *           *           *           *           *           *
ATA AGT GAA GAG GAT GAA CAT CAG TTT AAG TCT GAA AAG TCC TAT GTT AAG AAT TAC TAC AAG
TAT TCA CTT CTC CTA CTT GTA GTC AAA TTC AGA CTT TTC AGG ATA CAA TTC TTA ATG ATG TTC
 I   S   E   E   D   E   H   Q   F   K   S   E   K   S   Y   V   K   N   Y   Y   K>
```

FIG. 2C

METHODS FOR THE DIAGNOSIS OF FELINE INFECTIOUS ANEMIA

RELATED APPLICATIONS

The present application claims priority from U.S. Provisional Patent Application Ser. No. 60/059,551, filed Sep. 19, 1997, the disclosure of which is incorporated herein by reference.

BACKGROUND OF THE INVENTION

Feline infectious anemia (FIA) is a serious, and sometimes fatal, feline disease with worldwide distribution. The frequency of the disease has been difficult to estimate, due to difficulties detecting the causative agent, *Haemobartonella felis*. One study estimated that the causative agent was present in 7.5% of the ill cats studied and 3.6% of cats which appeared healthy, while another study reported infection rates as high as 23.2% in animals which had been referred for treatment. (Grindem, C. B. et al., "Risk Factors for *Haemobartonella felis* Infection in Cats," *JAVAM* 196:96 (1990); Nash, A. S. and Bobade, P. A., "*Haemobartonella felis* Infection in Cats from the Glasgow Area," *The Veterinary Record*, Oct. 11, 1986, page 373). Cats having low packed cell volume (PCV), a lack of vaccinations generally and against feline enteritis and respiratory tract virus infections specifically, catbite abscesses, a history of roaming outdoors and Feline Leukemia Virus (FeLV) positive status are at a greater risk for FIA. (Grindem et al., supra) Some studies have found a correlation between gender and risk of FIA, although other studies have failed to detect this association. (Hayes, H. M., "Feline Infectious Anaemia. Risk by Age, Sex, and Breed; Prior Disease; Seasonal Occurrence; Mortality," *J. Small Anim. Pract.* 14: 797 (1973)). Although the disease is curable by treatment with antibiotics, there is no induction of protective immunity. Infection may occur through a variety of routes, including ingestion of infected material, open wounds resulting from fighting, or transplacental transmission.

In addition to severe anemia, clinical manifestations of *Haemobartonella felis* infection include depression, weakness, anorexia, weight loss, paleness of mucous membranes, and, occasionally, splenomegaly. (Harvey, J. W. "Hemobartonellosis" in Clinical Microbiology and Infectious Diseases of the Dog and Cat, C. E. Greene Ed., W. B. Saunders Co. (1984)). Without intervention, approximately one third of cats with uncomplicated acute haemobartonellosis perish from severe anemia. (Holzworth, J. "Anemia in the Cat," *J. Am. Vet. Med. Assoc.*, 126:471–488, (1956); Splitter, E. J. et al.,"Feline Infectious Anemia," *Vet. Med.*, 51:17–22, (1956)). However, some cats experience both an immune response to the bacteria and a regenerative bone marrow response, which allows erythrocyte production to exceed erythrocyte destruction. These animals eventually recover from the disease, with the recovery time lasting one month or more. (Harvey, J. W. and Gaskin, J. M., "Experimental Feline Haemobartonellosis," *J. Am. Anim. Hosp. Assoc.*, 13:28–38, (1977)).

Unfortunately, cats that recover from acute infections with *Haemobartonella felis* remain infected with the pathogen for considerable time periods and may even remain infected throughout their lifetimes. (Splitter, E. J. et al. 1956, supra; Harvey, J. W. and Gaskin, J. M., "Feline Haemobartonellosis: Attempts to Induce Relapses of Clinical Disease in Chronically Infected Cats," *J. Am. Anim. Hosp. Assoc.*, 14:453–456, (1978)). In addition, carrier cats may not exhibit any symptoms of infection. The lack of observable symptoms increases the likelihood that the disease will escape treatment and that the carrier will transmit the organism to other animals.

*Haemobartonella felis* feeds and multiplies on the surface of red blood cells within the circulation, leading to progressive erythrocyte damage and shortened erythrocyte lifespans (Maede, Y., "Studies on Feline Haemobartonellosis. IV. Lifespan of Erythrocytes of Cats Infected with *Haemobartonella felis*," Jpn. J Vet. Sci., 37:269–272, (1975)). The anemia appears to result from the induction of autoantibodies which result in lysis of the host's own red blood cells. It has been hypothesized that bacterial attachment to the cell surface exposes hidden antigens on the surface or alters antigens normally expressed on the surface. The antibodies produced against the erythrocytes result in a false positive Coombs test.

An alternative hypothesis suggests that cell death is due to antibodies against *Haemobartonella felis*. It has been proposed that antibodies against *Haemobartonella felis* cause erythrocyte death by binding to bacteria on the surface of the cell and inducing complement fixation, thereby triggering lysis of the erythrocyte.

Following infection, the levels of bacteria found in the blood may rise and decline rapidly. (Maede, Y. and Hata, R., "Studies on Feline Haemobartonellosis. II. The Mechanism of Anemia Produced by Infection with *Haemobartonella felis*," Jpn. *J Vet. Sci.*, 37:49–54, (1975); Harvey and Gaskin, (1977), supra). This rapid and extensive fluctuation may be a consequence of splenic sequestration of infected erythrocytes and release of noninfected erythrocytes. (Maede, 1975, supra.).

Prior to the present invention, the most commonly employed method for detecting *Haemobartonella felis* infection relied on blood film staining. However, this approach suffers from numerous drawbacks. Because the bacteremia associated with *Haemobartonella felis* infection is episodic, it is often difficult to detect *Haemobartonella felis* using such traditional cytological approaches. In addition, the pleomorphic nature of *Haemobartonella felis* may cause the organism to be confused with stain precipitation or cellular debris. (C. B. Grindem et al. supra; C. M. R. Turner et al. Letters The Veterinary Record, Nov. 22, 1986 page 534; H. C. Carney and J. J. England, "Feline Hemobartonellosis," *Feline Infectious Diseases* 23: 79 (1993)).

Thus, there is a need for improved tests for *Haemobartonella felis* infection. In particular, given the low levels of *Haemobartonella felis* present during some stages of the disease, there is a need for sensitive diagnostics capable of detecting the low levels of circulating organisms present during some phases of the infection or in carrier cats harboring low residual levels of the organism. In addition, there is a need for selective tests capable of readily distinguishing *Haemobartonella felis* from other morphologically or genetically similar organisms. Finally, there is a need for tests which may be rapidly performed. The diagnostics described herein provide all of the preceding advantages.

SUMMARY OF THE INVENTION

The present invention relates to methods for detecting the presence of *Haemobartonella felis* in a mammal and isolated or purified nucleic acids containing at least 15 consecutive bases of the *Haemobartonella felis* 16S and/or 23S ribosomal RNA genes. In addition to being specific for *Haemobartonella felis*, the present assay provides high sensitivity due to the fact that the 16S and 23S ribosomal RNA genes or the transcripts thereof are present in multiple copies in the genome.

As used herein, the term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "purified" does not require absolute purity; rather, it is intended as a relative definition. In other words, "purified" means that the nucleic acid of the *Haemobartonella felis* 16S and/or 23S ribosomal RNA genes are enriched in concentration relative to other cellular components or nucleic acids. This enrichment is at least one order of magnitude, preferably two or three orders, and more preferably four or five orders of magnitude.

One aspect of the present invention is a method for detecting the presence of *Haemobartonella felis* in a mammal comprising obtaining a nucleic acid sample from a body fluid of said mammal, contacting said nucleic acid sample with at least one nucleic acid probe from the *Haemobartonella felis* 16S or 23S ribosomal RNA genes, said probe being specific for *Haemobartonella felis*; and determining whether said nucleic acid probe specifically hybridizes to said nucleic acid sample, wherein hybridization of said probe to said sample indicates that *Haemobartonella felis* is present in said mammal. In one embodiment, the probe comprises at least 15 consecutive nucleotides of the *Haemobartonella felis* 16S or 23S ribosomal RNA genes. In another embodiment, the probe is selected from the group consisting of the sequence of SEQ ID NO:3, a sequence fully complementary to the sequence of SEQ ID NO:3, a fragment comprising at least 15 consecutive nucleotides within the sequence of SEQ ID NO:3 and a fragment comprising at least 15 consecutive nucleotides of said sequence fully complementary to the sequence of SEQ ID NO:3. In a further embodiment, the mammal is a cat. In another embodiment, the nucleic acid sample comprises a DNA sample. In another embodiment, the contacting step comprises contacting said nucleic acid sample with a labeled probe and said determining step comprises detecting whether said labeled probe hybridizes to said nucleic acid sample. In another embodiment, the contacting step comprises performing a method selected from the group consisting of in situ hybridization, Southern blotting, Northern blotting, and dot blotting.

Another aspect of the present invention is a method for detecting the presence of *Haemobartonella felis* in a mammal comprising obtaining a nucleic acid sample from said mammal, contacting said nucleic acid sample with a first primer and a second primer, wherein at least one of said first and second primers comprises a sequence of at least 15 consecutive bases contained within SEQ ID NO:3 or a sequence fully complementary thereto, and conducting an amplification reaction with said first and second primers, wherein an amplification product will be observe if said nucleic acid sample contains nucleic acid from *Haemobartonella felis*. In one embodiment, both said first primer and said second primer are contained within SEQ ID NO:3 or a sequence fully complementary thereto. In another embodiment, the first primer is contained within the sequence of SEQ ID NO:3 or a sequence fully complementary thereto and said second primer is contained within a sequence outside the sequence of SEQ ID NO:3. In a further embodiment, the sequence outside the sequence of SEQ ID NO:3 is the *Haemobartonella felis* 5S ribosomal RNA gene. In another embodiment, the first primer comprises the sequence of SEQ ID NO:4 and said second primer comprises the sequence of SEQ ID NO:5. In a further embodiment, the first primer comprises the sequence of SEQ ID NO:6 and said second primer comprises the sequence of SEQ ID NO:7.

Another aspect of the present invention is an isolated or purified nucleic acid comprising the sequence of SEQ ID NO:3 or a sequence fully complementary thereto. In one embodiment, the nucleic acid comprises at least 15 consecutive bases of the sequence of SEQ ID NO:3 or a sequence fully complementary thereto. In another embodiment, the nucleic acid has a length less than about 1800 base pairs.

Another aspect of the present invention is a vector comprising at least 15 consecutive bases of the sequence of SEQ ID NO:3 or a sequence fully complementary thereto.

Another aspect of the present invention is a nucleic acid oligomer having a sequence selected from the group consisting of SEQ ID NO:4, SEQ ID NO:5, SEQ ID NO:6, SEQ ID NO:7, and the sequences complementary to SEQ ID NO:4, SEQ ID NO:5, SEQ ID NO:6, and SEQ ID NO:7.

Another aspect of the present invention is an isolated or purified nucleic acid comprising at least 15 consecutive bases of the sequence of SEQ ID NO: 10 or a sequence fully complementary thereto.

Another aspect of the present invention is an isolated or purified nucleic acid comprising at least 15 consecutive bases of the sequence of nucleotides 3–77 of SEQ ID NO: 10 or a sequence fully complementary thereto.

Another aspect of the present invention is an isolated or purified nucleic acid comprising at least 15 consecutive bases of the sequence of nucleotides 81–362 of SEQ ID NO: 10 or a sequence fully complementary thereto.

Another aspect of the present invention is an isolated or purified nucleic acid comprising at least 15 consecutive bases of the sequence of nucleotides 366–416 of SEQ ID NO: 10 or a sequence fully complementary thereto.

Another aspect of the present invention is an isolated or purified nucleic acid comprising at least 15 consecutive bases of the sequence of nucleotides 420–941 of SEQ ID NO: 10 or a sequence fully complementary thereto.

Another aspect of the present invention is an isolated or purified nucleic acid comprising at least 15 consecutive bases of the sequence of nucleotides 945–977 of SEQ ID NO: 10 or a sequence fully complementary thereto.

Another aspect of the present invention is an isolated or purified polypeptide comprising a sequence selected from the group consisting of SEQ ID NO: 11, SEQ ID NO: 12, SEQ ID NO: 13, and SEQ ID NO: 15. In one embodiment, the isolated or purified polypeptide is a fragment of a sequence selected from the group consisting of SEQ ID NO: 11, SEQ ID NO: 12, SEQ ID NO: 13, and SEQ ID NO: 15 comprising an antigenic epitope.

Another aspect of the present invention is an isolated or purified polypeptide comprising the sequence of SEQ ID NO: 14.

Another aspect of the present invention is an isolated or purified fragment of the polypeptide of SEQ ID NO: 14, said fragment comprising an antigenic epitope.

Another aspect of the present invention is an isolated or purified antibody capable of specifically binding a polypeptide comprising a sequence selected from the group consisting of SEQ ID NO:11, SEQ ID NO:12, SEQ ID NO:13, and SEQ ID NO: 15.

Another aspect of the present invention is an isolated or purified antibody capable of specifically binding a polypeptide comprising the sequence of SEQ ID NO:14 or a fragment thereof comprising an antigenic epitope.

Another aspect of the present invention is a method for detecting the presence of *Haemobartonella felis* in a mammal comprising the steps of obtaining a sample of a bodily fluid from said mammal, contacting said sample with an antigen encoded by the sequence of SEQ ID NO: 10 or a fragment thereof comprising an antigenic epitope, said antigen being recognized by antibodies in serum, plasma, or blood from a mammal infected with *Haemobartonella felis* but not by antibodies in serum, plasma, or blood from an uninfected mammal, and determining whether antibodies in said sample bind to said antigen. In one embodiment, the antigen is a polypeptide selected from the group consisting of the polypeptides of SEQ ID NO: 11, SEQ ID NO: 12, SEQ ID NO: 13, SEQ ID NO: 15 and fragments thereof comprising an antigenic epitope. In another embodiment, the antigen is selected from the group consisting of the polypeptide of SEQ ID NO: 14 and fragments thereof comprising an antigenic epitope.

Another aspect of the present invention is an apparatus comprising a polypeptide attached to a solid support wherein said polypeptide is selected from the group consisting of the polypeptides of SEQ ID NO: 11, SEQ ID NO: 12, SEQ ID NO: 13, SEQ ID NO: 15 and fragments thereof comprising an antigenic epitope.

Another aspect of the present invention is an apparatus comprising a polypeptide attached to a solid support wherein said polypeptide is selected from the group consisting of the polypeptide of SEQ ID NO: 14 and fragments thereof comprising an antigenic epitope.

Another aspect of the present invention is a method of inducing an immune response against *Haemobartonella felis* in a mammal comprising the steps of obtaining a polypeptide encoded by SEQ ID NO: 10 or a fragment thereof, said polypeptide comprising an antigenic epitope and administering said polypeptide or fragment to said mammal in an amount sufficient to induce said immune response. In one embodiment, the polypeptide or fragment is selected from the group consisting of the polypeptides of SEQ ID NO: 11, SEQ ID NO: 12, and SEQ ID NO: 13, SEQ ID NO: 15 and fragments thereof comprising an antigenic epitope. In another embodiment, the polypeptide or fragment is the polypeptide of SEQ ID NO: 14 or a fragment thereof comprising an antigenic epitope.

Another aspect of the present invention is a method for inducing an immune response against *Haemobartonella felis* in a mammal comprising the steps of growing a culture of *Haemobartonella felis*, killing or inactivating the *Haemobartonella felis* cells in said culture, and administering said killed or inactivated *Haemobartonella felis* cells to said mammal. In one embodiment, said growing step comprises the steps of obtaining *Haemobartonella felis* cells introducing said cells into medium comprising feline blood and TSB broth supplemented with ascorbic acid and glutathione and incubating said cells under conditions which permit said cells to replicate.

Another aspect of the present invention is a method for detecting the presence of *Haemobartonella felis* in a mammal comprising the steps of obtaining a sample of a bodily fluid from said mammal, contacting said sample with an antigen from Mycoplasma, said antigen from Mycoplasma being an antigen which is recognized by antibodies in serum, plasma, or blood from mammals infected with *Haemobartonella felis* but not by antibodies in serum, plasma, or blood from mammals which are not infected with *Haemobartonella felis*, and determining whether said antibodies in said sample bind to said antigen from Mycoplasma. In one embodiment, the antigen from Mycoplasma comprises the pMGA protein of *Mycoplasma gallisepticum* or a fragment thereof containing an antigenic epitope. In another embodiment, the antigen comprises the pMGA 1.1 protein of the strain of *Mycoplasma gallisepticum* having the ATCC deposit number 19610 or a fragment thereof containing an antigenic epitope.

Another aspect of the present invention is an apparatus comprising a polypeptide attached to a solid support wherein said polypeptide is an antigen from Mycoplasma, said antigen from Mycoplasma being an antigen which is recognized by antibodies in serum, plasma, or blood from mammals infected with *Haemobartonella felis* but not by antibodies in serum, plasma, or blood from mammals which are not infected with *Haemobartonella felis*. In one embodiment, the antigen from Mycoplasma comprises the pMGA protein of *Mycoplasma gallisepticum* or a fragment thereof containing an antigenic epitope. In another embodiment, the antigen from Mycoplasma comprises the pMGA protein of the strain of *Mycoplasma gallisepticum* having the 1.1 deposit number 19610 or a fragment thereof containing an antigenic epitope.

Another aspect of the present invention is a method for detecting the presence of *Haemobartonella felis* in a mammal comprising the steps of growing a culture of Mycoplasma cells, said Mycoplasma cells expressing an antigen which is recognized by antibodies in serum, plasma, or blood from mammals infected with *Haemobartonella felis* but not by antibodies in serum, plasma, or blood from mammals which are not infected with *Haemobartonella felis*, fixing said antigen to a solid support, contacting said solid support with a sample of a bodily fluid from said mammal and determining whether antibodies in said sample bind to said antigen from Mycoplasma. In one embodiment, the culture comprises a culture of *Mycoplasma gallisepticum*.

Another aspect of the present invention is a method of inducing an immune response against *Haemobartonella felis* in a mammal comprising the steps of administering a composition comprising an antigen expressed by Mycoplasma cells which is recognized by antibodies in serum, plasma, or blood from mammals infected with *Haemobartonella felis* but not by antibodies in serum, plasma, or blood from mammals which are not infected with *Haemobartonella felis* to said mammal in an amount sufficient to induce said immune response. In one embodiment, the antigen is expressed by *Mycoplasma gallisepticum*. In another embodiment, the administering step comprises administering a composition comprising a killed preparation or avirulent preparation of *Mycoplasma gallisepticum* to said mammal. In a further embodiment, the administration step comprises administering a composition comprising a preparation enriched for said antigen to said mammal. In another embodiment, the antigen comprises the pMGA protein. In a further embodiment, the antigen comprises the pMGA 1.1 protein of the strain of *Mycoplasma gallisepticum* having the ATCC deposit number 19610 or a fragment thereof comprising an antigenic epitope.

Another aspect of the present invention is a method for inducing an immune response against *Haemobartonella felis* in a mammal comprising the steps of growing a culture of Mycoplasma, and administering the cells in said culture to said mammal. In one embodiment, the method further comprises killing or inactivating said Mycoplasma cells. In another embodiment, the culture comprises a culture of *Mycoplasma gallisepticum*. In a further embodiment, the culture is a culture of the strain of *Mycoplasma gallisepticum* having the ATCC deposit number 19610.

BRIEF DESCRIPTION OF THE DRAWINGS

FIG. 1 shows the sequences of the *Haemobartonella felis* 16S ribosomal RNA gene and *Haemobartonella felis* 23S ribosomal RNA genes.

FIG. 2 shows a genomic sequence from *Haemobartonella felis* which lies outside of the ribosomal RNA genes.

DETAILED DESCRIPTION OF THE PREFERRED EMBODIMENT

Prior to the present invention, the genome of *Haemobartonella felis* was poorly characterized. Accordingly, there was a need for further sequence information, and, in particular, for sequence information which could be utilized in rapid, sensitive, and specific diagnostic techniques. The present invention relates to specific detection methods based on detection of the *Haemobartonella felis* 16S and 23S ribosomal RNAs themselves or the genes encoding the 16S and 23S ribosomal RNAs, each of which contain sequences which are highly variable between species.

Another aspect of the present invention is a nucleic acid obtained from *Haemobartonella felis* which includes several open reading frames, polypeptides encoded by the open reading frames, antibodies against the polypeptides, and diagnostic techniques using these polypeptides.

The present invention also relates to methods for culturing *Haemobartonella felis* and methods for using the cultured organism in vaccines or to identify nucleic acids encoding polypeptides useful in diagnostic methods.

The 16S and 23S ribosomal RNA genes of *Haemobartonella felis* were cloned as described in Example 1 below.

EXAMPLE 1

Isolation and Sequencing of Clones Encoding the *Haemobartonella felis* 16S Ribosomal RNA The sequence of the *Haemobartonella felis* 5S ribosomal RNA gene, was retrieved from the GenBank Sequence Data Base Los Alamos National Laboratory, New Mexico, U.S.A. Based on the presumptive proximity of the 5S ribosomal RNA gene to the 16S and 23S ribosomal RNA genes, a polymerase chain reaction (PCR) was performed using a specific primer (DT-15) to "anchor" in the 5S ribosomal RNA gene and a non-stringent primer (16S.02) targeted to the 16S ribosomal RNA gene. The 16S.02 primer was prepared based on a consensus of sequences within the 16S ribosomal RNA genes of a collection of Bartonella-like organisms. The 16S.02 primer sequence was selected because it lies in a conserved region of the 16S ribosomal genes of Bartonella-like organisms which was likely to be present in the *Haemobartonella felis* 16S ribosomal RNA gene.

The sequences of DT-15 and the non-stringent primer, 16S.02, are as follows:

DT-15: 5'-GACTTGGTGGTTATGGCG-3' (SEQ ID NO:1)

16S.02: 5'-CATGAGGACTTGACGTCATC-3' (SEQ ID NO:2)

PCR was run under non-stringent conditions using DNA obtained from the blood of 6 cats suffering from FIA as evidenced by clinical anemia and cytological analysis. The DNA was obtained from the infected cats by lysing 100 μl of whole blood and passing the lysate through a DNA binding column available from Qiagen. As controls, DNA samples obtained from the blood of six normal cats were subjected to PCR at the same time and using identical conditions. The PCR reaction was performed as follows.

| Time (min.) | Temp (° C.) | Cycles |
|---|---|---|
| 1.5 | 94 | 1 |
| 0.5 | 94 | |
| 1.5 | 52 | 40 |
| 0.5 | 72 | |
| 10 | 72 | 1 |

An amplicon of 466 bp was observed with the DNA of all six of the *Haemobartonella felis*-infected cats, while no such amplification product was found in samples from the uninfected cats. The amplicon was inserted into the pCR2.1 vector (Invitrogen Corp., Carlsbad, Calif. 92008), a cloning vector having multiple restriction sites therein for inserting and sequencing the amplicon, and the sequence of the insert was determined.

The insert was confirmed to be part of the 16S ribosomal RNA gene by comparing it to the analogous sequences from the related rickettsial organisms *Bartonella henselae* and *Afipia felis* using the method of Wilbur and Lipman, Rapid Similarity Searches of Nucleic Acid and Protein Data Banks, *Proc. Nat. Acad. Sci. U.S.A.* 80:726–730 (1983) and the MacVector DNA analysis software available from the Oxford Molecular Group. Using this approach, 72% and 73% homology was found between the sequence of the insert and the sequences of the *Bartonella henselae* and *Afipia felis* 16S ribosomal RNA genes. A similar comparison between the recovered sequence and that of the 5S ribosomal RNA of *Haemobartonella felis* found no significant homology. These results demonstrate that the recovered sequence is in fact the 16S ribosomal RNA gene of *Haemobartonella felis* and, that it is uncontaminated by sequences of the adjacent 5S ribosomal RNA gene.

The 466 bp amplicon obtained using the above procedure was used to clone and sequence the 16S and 23S ribosomal RNA genes. Sequencing was performed using an ABI Model 377 automatic sequenator.

The sequences of the 16S and 23S ribosomal RNA genes (SEQ ID NO:3 and its complementary strand) are given in FIG. 1, in which Y indicates that the base is C or T and R indicates that the base is A or G. FIG. 1 also indicates the start and end points of the 16S and 23S ribosomal RNA sequences.

The 16S and/or 23S ribosomal RNA genes or fragments thereof may be inserted into vectors designed to replicate in prokaryotic or eukaryotic host cells and introduced into the host cells using transformation or transfection techniques such as those described in Sambrook et al., Molecular Cloning: A Laboratory Manual, Cold Spring Harbor Laboratory Press, 1989, which is incorporated herein by reference. The vectors may be RNA vectors or DNA vectors.

As described in Examples 2 and 3 below, the sequence of SEQ ID NO:3 can be used to design and identify oligonucleotides which are capable of specifically detecting the presence of the *Haemobartonella felis* 16S or 23S ribosomal RNA genes or their transcripts (the 16S ribosomal RNA or the 23S ribosomal RNAs) in a sample, such as a nucleic acid sample from a subject to be tested for infection with *Haemobartonella felis*.

EXAMPLE 2

Design of Primers Capable of Specifically Detecting the *Haemobartonella felis* 16S Ribosomal RNA Gene The sequence of the 16S ribosomal RNA gene determined above was used to design two primer pairs capable of specifically detecting the presence of the *Haemobartonella felis* 16S ribosomal RNA gene or its transcript (the 16S ribosomal RNA itself) when used in PCR reactions. These two primer pairs, FIA-11/12 and FIA-13/14, amplify a fragment internal to the 16S ribosomal RNA gene. The sequences of these primers are as follows.

FIA-11: 5'-CTCTTTAGACAAGTAACTAAAGAG-3' (SEQ ID NO:4)

FIA-12: 5'-CAAATGGGATTAGRTACCCC-3' (SEQ ID NO:5)

FIA-13: 5'-GTCACCTCGATAACCTCTAC-3' (SEQ ID NO:6)

FIA-14: 5'-CTTTAGTGTTGTAGCTTACGC-3' (SEQ ID NO:7)

The positions of these primers within the 16S ribosomal RNA gene are shown by the boxes in FIG. 1.

The optimal conditions for PCR analysis with the above primer pairs are as follows:

(a) Primer concentrations: 2 ng of each primer per 50 µl of total volume mix.

(b) The optimal PCR temperature and time cycles are given in the following program:

| Time (min.) | Temp (° C.) | Cycles |
|---|---|---|
| 1.5 | 94 | 1 |
| 0.5 ⎫ | 94 ⎫ | |
| 1.5 ⎬ | 56 ⎬ | 40 |
| 0.75 ⎭ | 72 ⎭ | |
| 10 | 72 | 1 |

The above primer pairs were screened for specificity for *Haemobartonella felis* as follows. A PCR analysis was run on DNA samples obtained from the blood of cats which were infected with *Haemobartonella felis* and control cats which were not infected with *Haemobartonella felis*. In addition, a PCR analysis was also run on DNA samples prepared from culture-cloned colonies of two other rickettsial-like blood borne parasites of cats, *Bartonella henselae* and *Afipia felis*. Following the PCR analysis, amplicons were observed in the DNA samples from animals infected with *Haemobartonella felis* but not in samples from the control animals or from the other rickettsial-like organisms. The amplicons obtained were the expected sizes of 355 bp for FIA-11/12 and 194 bp for FIA-13/14. Thus, the tested primers are specific for the *Haemobartonella felis* 16S ribosomal RNA gene or its transcript and can be used to detect the presence of these nucleic acids in a nucleic acid sample such as a sample from a subject to be tested for infection with *Haemobartonella felis*.

EXAMPLE 3

Design of Primers Capable of Specifically Detecting the *Haemobartonella felis* 23S Ribosomal RNA Gene The sequence of the 23S ribosomal RNA gene determined above was used to design a primer pair capable of specifically detecting the presence of the *Haemobartonella felis* 23S ribosomal RNA gene or its transcript (the 23S ribosomal RNA itself) when used in PCR reactions. This primer pair, FIA-21/FIA-22 amplifies a fragment internal to the 23S ribosomal RNA gene.

The sequences of these primers are as follows.

FIA-21: 5' CCATCGACTACGCCTCTC 3'. (SEQ ID NO:8)

FIA-22: 5' TTTATGGCTAATGGCGTGCG3'. (SEQ ID NO:9)

PCR reactions were conducted on 8 clinical DNA samples from cats infected with *Haemobartonella felis* using the FIA-11/FIA-12 primer pair from the 16S ribosomal RNA gene or the FIA-21/FIA-22 primer pair from the 23S ribosomal RNA gene. The concentration of reagents and the thermocycler program for each of the primer pairs were as described in Example 2 above.

A 23S ribosomal RNA amplicon was observed in most of the samples in which a 16S ribosomal RNA amplicon was obtained. The tested primers are specific for the *Haemobartonella felis* 23S ribosomal RNA gene or its transcript and can be used to detect the presence of these nucleic acids in a nucleic acid sample such as a sample from a subject to be tested for infection with *Haemobartonella felis*.

Primer pairs derived from the 23S ribosomal RNA gene sequence which are specific for *Haemobartonella felis* can be identified as described in Example 2.

Thus, the 16S ribosomal RNA gene or its transcript, the 23S ribosomal RNA gene or its transcript, or both genes or their transcripts may be used as targets for specific amplification and detection of *Haemobartonella felis* by PCR or other hybridization based techniques.

In such procedures, a nucleic acid sample is obtained from a mammal. The nucleic acid is then contacted with at least one probe specific for *Haemobartonella felis* containing at least 15 nucleotides from the sequence of SEQ ID NO:3. Hybridization of the probe to the nucleic acid sample is then assayed. Hybridization of the probe to the sample indicates that the sample contains nucleic acid from *Haemobartonella felis*.

Other primer pairs based on SEQ ID NO:3 may also be used to specifically detect the presence of the *Haemobartonella felis* 16S and/or 23S ribosomal RNA genes or their transcripts by PCR. For example, primers comprising sequences contained within the sequence of SEQ ID NO:3 or complementary to the sequence of SEQ ID NO:3 may be synthesized using conventional techniques. The primers may be screened to determine which primer pairs are capable of specifically detecting the *Haemobartonella felis* 16S and/or 23S ribosomal RNA genes or their transcripts (the 16S or 23S ribosomal RNAs) using the procedure of Example 2.

The primers used in the PCR reaction comprise at least 15 consecutive nucleotides within the sequence of SEQ ID NO:3 or the sequence complementary thereto. Preferably, the primers comprise fragments between 15 and 25 consecutive nucleotides within the sequence of SEQ ID NO:3 or the sequence complementary thereto.

The primers may be within or complementary to any region within the sequence of SEQ ID NO:3. In some embodiments, both members of the primer pair may be within the 16S ribosomal RNA gene. In other embodiments, both members of the primer pair may be within the 23S ribosomal RNA gene. In additional embodiments, one member of the primer pair may be within the 16S ribosomal RNA gene and the other member of the primer pair may be between the 16S ribosomal RNA gene and the 23S ribosomal RNA gene. In yet another embodiment, one primer may be within the 23S ribosomal RNA gene and the other member of the primer pair may be between the 23S ribosomal RNA gene and the 16S ribosomal RNA gene. In a further embodiment, both members of the primer pair may be within the sequence between the 16S and 23S ribosomal RNA genes. In yet another embodiment, one member of the primer pair may be within the 16S ribosomal RNA gene and the other member may be within the 23S ribosomal RNA gene. In some embodiments, the presence of nucleic acid from *Haemobartonella felis* in a sample may be detected using two primer pairs each of which is capable of specifically detecting the presence of nucleic acid from *Haemobartonella felis* in a sample. In some embodiments, the two primer pairs may be both be located in the 16S ribosomal RNA gene. In other embodiments, the two primer pairs may be both be located in the 23S ribosomal RNA gene. In some embodiments, one primer pair may be within the 16S ribosomal RNA gene and the other primer pair may be within the 23S ribosomal RNA gene. It will be appreciated that the primer pairs may be located at any set of positions within the sequence of SEQ ID NO:3 which permits specific detection of the 16S and/or the 23S ribosomal RNAs from *Haemobartonella felis*.

Primer pairs capable of specifically detecting nucleic acid encoding the *Haemobartonella felis* 16S or 23S ribosomal RNAs or the 16S or 23S ribosomal RNAs themselves may also comprise one primer contained within the sequence of SEQ ID NO:3 or the sequence complementary thereto and one primer derived from a sequence outside of the sequence of SEQ ID NO:3. In embodiments in which one of the primers is outside of the sequence of SEQ ID NO:3, it is preferred that the distance between the sequences to which the primers hybridized is at least about 100 bases. More preferably, the distance between the sequences to which the primers hybridize is about 100–200 bases. In a highly preferred embodiment, the distance between the sequences to which the primers hybridize is about 300–500 bases. In one version of this embodiment, one of the primers may be derived from the *Haemobartonella felis* 5S ribosomal RNA sequence. In particular, the primer derived from the 5S ribosomal RNA sequence may comprise the DT-15 primer described above.

Preferably, the sequences to which the primers hybridize are at least about 100 bases apart, such that the resulting amplicon is at least about 100 bases in length. More preferably, the primers hybridize to sequences which are 100–200 bases apart. In a highly preferred embodiment the primers hybridize to sequences which are between about 200 and about 450 bases apart.

For example, one of the primers may hybridize between position 903 and position 927 of the sequence of FIG. 1 and SEQ ID NO:3 and the other primer may hybridize between position 573 and position 592. Alternatively, one primer may hybridize between position 639 and position 659 of the sequence of FIG. 1 and SEQ ID NO:3 and the other primer may hybridize between position 813 and position 832.

As those skilled in the art will appreciate, the PCR regimen may readily be varied for the primer pairs being tested in order to determine the optimal parameters for the particular primer pair being analyzed. Accordingly, the present invention may be used to specifically detect the *Haemobartonella felis* 16S and/or 23S ribosomal RNA genes or their transcripts (the 16S and 23S ribosomal RNAs) by amplifying a variety of fragments within the *Haemobartonella felis* 16S and/or 23S ribosomal RNA genes which are specific to *Haemobartonella felis*. Those of skill in the art will appreciate that the amplification reaction may be conducted on nucleic acid samples containing DNA, RNA, or both using conventional PCR techniques such as those described in Sambrook et al., supra.

In addition to the PCR based detection techniques described above, it will be appreciated that any of the nucleic acid amplification techniques familiar to those skilled in the art may also be used to detect the presence of the *Haemobartonella felis* 16S and/or 23S ribosomal RNAs or the 16S and/or 23S ribosomal RNA genes in a sample. These techniques include ligase chain reaction, 3SR, and strand displacement. (See Barany, F., "The Ligase Chain Reaction in a PCR World", *PCR Methods and Applications* 1:5–16 (1991); E. Fahy et al., "Self-sustained Sequence Replication (3SR): An Isothermal Transcription-based Amplification System Alternative to PCR", *PCR Methods and Applications* 1:25–33 (1991); and Walker G. T. et al., "Strand Displacement Amplification-an Isothermal in vitro DNA Amplification Technique, *Nucleic Acid Research* 20:1691–1696 (1992) the disclosures of which are incorporated herein by reference in their entireties).

In addition to diagnosing the presence of *Haemobartonella felis*, the present invention may also be used to monitor the course of infection or the effectiveness of treatment as described in Example 4.

EXAMPLE 4

PCR Based Analysis of Disease Progression

PCR reactions were performed as in Example 2 using DNA samples from an uninfected cat, an infected cat prior to antibiotic treatment, the same infected cat 11 days after antibiotic treatment was commenced, and a positive control. The expected amplicon was detected in the positive control sample and the sample from the infected cat taken prior to initiation of the antibiotic treatment. The amplicon was not detected in the control sample or in the sample taken from the infected cat 11 days following commencement of antibiotic treatment. Thus, the course of infection or the effectiveness of treatment can be followed by using the diagnostics of the present invention to monitor the number of infectious organisms harbored by the infected animal.

As described below in Example 5, probes comprising sequences contained within the sequence of SEQ ID NO:3 or sequences complementary thereto may also be used to detect the presence of the *Haemobartonella felis* 16S and/or 23S ribosomal RNA genes or their transcripts (the 16S and 23S ribosomal RNAs) in nucleic acid samples using techniques other than the polymerase chain reaction.

In some embodiments of the present invention, described in Example 5 below, a probe, such as a labelled probe comprising the sequence of SEQ ID NO:3 or the sequence complementary thereto, or fragments thereof, is hybridized to nucleic acid samples and hybridization of the probe to the sample is directly detected. For example, these embodiments may employ procedures such as the in situ hybridization, Southern blotting, Northern blotting, or dot blotting techniques, described in Sambrook et al., supra and P. Michael Conn, *Gene Probes,* Academic Press, 1989, which are incorporated herein by reference.

EXAMPLE 5

Use of Probes Derived From the Sequence of SEQ ID NO:3 to Detect the Presence of the *Haemobartonella felis* 16S and/ or 23S Ribosomal RNA Genes or Their Transcripts In direct detection techniques such as in situ hybridization, Southern blotting, Northern blotting, dot blotting, or pre-gel hybridization, a probe is labeled with detectable agents such as radioisotopes or fluorescent tags. For example, the probe may be labeled using polynucleotide kinase, nick translation, or in vitro transcription as described in Sambrook et al., supra. Alternatively, the probe may be a peptide nucleic acid oligomer labeled with a chemiluminescent agent as described in Perry-O'Keefe et al., "Peptide Nucleic Acid Pre-gel Hybridization: An Alternative to Southern Hybridization", *Proc. Natl. Acad. Sci.* 93:14670–14675 (1996), the disclosure of which is incorporated herein by reference. Preferably, the probe fragments comprise at least 15 consecutive nucleotides or nucleotide analogs contained within the sequence of SEQ ID NO:3 or the sequence complementary thereto. More preferably, the fragments comprise at least about 100 consecutive nucleotides contained within the sequence of SEQ ID NO:3 or the sequence complementary thereto. In another preferred embodiment, the probes comprise at least about 200 consecutive nucleotides contained within the sequence of SEQ ID NO:3. In some embodiments, the probes comprise the sequences of SEQ ID NO:4, SEQ ID NO:5, SEQ ID NO:6, SEQ ID NO:7, SEQ ID NO:8 or SEQ ID NO:9 or sequences complementary thereto as well as peptide nucleic acid oligomers having the base sequences of SEQ ID NO:4, SEQ ID NO:5, SEQ ID NO:6, SEQ ID NO:7, SEQ ID NO:8 or SEQ ID NO:9 or sequences complementary thereto.

In each of the techniques listed above, the specificity of the probes for the *Haemobartonella felis* 16S or 23S ribosomal RNA genes or their transcripts can be determined by screening candidate probes to identify probes which hybridize to samples containing the *Haemobartonella felis* 16S or 23S ribosomal RNA genes or their transcripts but not to control samples lacking the *Haemobartonella felis* 16S or 23S ribosomal RNA genes or their transcripts or to control samples containing the 16S or 23S ribosomal RNA genes or their transcripts from related rickettsia-like pathogens such as *Bartonella henselae* and *Afipia felis*.

Similarly for each of the techniques, appropriate hybridization and wash conditions can be determined by varying the hybridization and wash temperatures and the ionic strengths of the hybridization and wash solutions to determine which conditions yield hybridization in samples which contain the *Haemobartonella felis* 16S or 23S ribosomal RNA genes or their transcripts but not in control samples lacking the *Haemobartonella felis* 16S or 23S ribosomal RNA genes or their transcripts or in control samples containing the 16S or 23S ribosomal RNA genes (or transcripts thereof) from related rickettsia-like pathogens such as *Bartonella henselae* and *Afipia felis*.

As used herein, the term "hybridization" means that the probe associates with the target nucleic acid specifically and does not associate with non-target nucleic acids which have limited homology to the target sequence. Preferably, the hybridization is conducted under conditions which require 100% identity between the probe and the target nucleic acid, at least 95% identity between the probe and the target nucleic acid or at least 90% identity between the probe and the target nucleic acid. However, it will be appreciated that the hybridization may be conducted under any conditions in which the probe will hybridize to the target *Haemobartonella felis* sequence but not to non-target sequences present in the sample.

Procedures for Southern blotting, Northern blotting, and dot blotting are described in Sambrook et al., supra. Briefly, to perform a Southern, Northern, or dot blot hybridization, a nucleic acid sample to be tested for *Haemobartonella felis* is obtained from the subject organism. In Northern or Southern blots, the sample is run on an agarose gel and transferred to a nitrocellulose or nylon membrane through capillary action, electrophoresis, or vacuum application, as described in Sambrook et al., supra. In dot blots, the nucleic acid sample is spotted on the membrane.

The nucleic acid is then fixed to the membrane. After soaking the membrane with prehybridization solution, the membrane is contacted with hybridization solution containing the labeled probe and incubated to allow the probe to hybridize to any samples which contain the *Haemobartonella felis* 16S and/ or 23S ribosomal RNA genes or their transcripts. The membrane is then washed with wash solution to remove any probe which is non-specifically bound to the membrane. The filter is then autoradiographed to detect specifically bound probe.

In situ hybridization procedures are described in Conn, supra. Briefly, to perform in situ hybridization a tissue sample or cellular sample to be tested is fixed. The samples are prehybridized, washed, and allowed to air dry. Once dry, the sample is contacted with a probe in hybridization solution, washed and autoradiographed.

Pre-gel hybridization using peptide nucleotide oligomers is described in Perry-O'Keefe et al., "Peptide Nucleic Acid Pre-gel Hybridization: An Alternative to Southern Hybridization", *Proc. Natl. Acad. Sci.* 93:14670–14675 (1996). Briefly, a peptide nucleic acid oligomer is hybridized in solution to denatured nucleic acid which potentially contains the *Haemobartonella felis* 16S and/or 23S ribosomal RNA sequences (or the transcripts thereof) at low ionic strength. The hybridization reaction is then subjected to gel electrophoresis. Peptide nucleic acid oligomers which have not hybridized to nucleic acid containing the 16S and/or 23S ribosomal RNA sequences do not migrate into the gel. However, peptide nucleic acid oligomers which have hybridized to the nucleic acid in the sample do migrate into the gel and are detectable by chemiluminescence or autoradiography.

To determine whether a mammal is infected with *Haemobartonella felis*, tissue or nucleic acid samples are obtained and hybridization is performed as described above using at least one probe specific for *Haemobartonella felis*. If desired, more than one probe may be used. Where more than one probe is used, the probes may be within the 16S ribosomal RNA gene, the 23S ribosomal RNA gene, the sequence between the 16S and 23S ribosomal RNA genes, or any combination thereof. Hybridization of the probe to the nucleic acid sample indicates that the *Haemobartonella felis* 16S and/or 23S ribosomal RNA genes or their transcripts (the 16S and 23S ribosomal RNAs) are present in the sample.

The method of inverse PCR was employed to gene-walk upstream and downstream from the 23S rRNA gene. DNA from *H. felis* infected blood was purified and samples were separately treated with different restriction enzymes. After ligation, the non-23S rRNA portion of the circularized DNA was PCR amplified using primers complimentary to those used for amplifying the 23S rRNA portion of the genome. The resulting amplicon, which contained a portion of the genome of *Haemobartonella felis* which lies outside of the region that codes for the ribosomal RNAs, was then cloned and sequenced. The resulting sequence, SEQ ID NO:10, and the sequence of its complementary strand are shown in FIG. 2, along with the sequences of the polypeptides encoded thereby.

SEQ ID NO:10 contains five open reading frames (ORFs), which presumptively code for peptides or proteins. ORF 1 (nucleotides 3–77 of SEQ ID NO:10) encodes a polypeptide of 25 amino acids (SEQ ID NO:11). ORF 2 (nucleotides 81 through 362 of SEQ ID NO:10) encodes a polypeptide of 94 amino acids (SEQ ID NO:12). ORF 3 (nucleotides 366–416 of SEQ ID NO:10) encodes a polypeptide of 17 amino acids (SEQ ID NO:13). ORF 4 (nucleotides 420–941 of SEQ ID NO:10) encodes a polypeptide of 174 amino acids (SEQ ID NO:14). ORF 5 (nucleotides 945–977 of SEQ ID NO:10) encodes a polypeptide of 11 amino acids (SEQ ID NO:15).

Sequences within the sequence of SEQ ID NO:10 which are able to specifically identify animals infected with *Haemobartonella felis* may be designed and identified using the screening procedures set forth above. These sequences can be used in any of the nucleic acid based diagnostic techniques discussed above with regard to the 16S and 23S ribosomal RNA genes.

Accordingly, one aspect of the present invention is an isolated or purified nucleic acid comprising the sequence of SEQ ID NO: 10 or a fragment comprising at least 10, at least 15, at least 20, at least 25, at least 40, or more than 40 consecutive bases of the sequence of SEQ ID NO: 10. Another aspect of the present invention an isolated or purified nucleic acid comprising nucleotides 3–77 of SEQ ID NO:10 or a fragment comprising at least 10, at least 15, at least 20, at least 25, at least 40, or more than 40 consecutive bases of this nucleic acid. Another aspect of the present invention an isolated or purified nucleic acid comprising nucleotides 81–362 of SEQ ID NO:10 or a fragment comprising at least 10, at least 15, at least 20, at least 25, at least 40, or more than 40 consecutive bases of this nucleic acid. Another aspect of the present invention an isolated or purified nucleic acid comprising nucleotides 366–416 of SEQ ID NO:10 or a fragment comprising at least 10, at least 15, at least 20, at least 25, at least 40, or more than 40 consecutive bases of this nucleic acid. Another aspect of the present invention an isolated or purified nucleic acid comprising nucleotides 420–941 of SEQ ID NO: 10 or a fragment comprising at least 10, at least 15, at least 20, at least 25, at least 40, or more than 40 consecutive bases of this nucleic acid. Another aspect of the present invention an isolated or purified nucleic acid comprising nucleotides 945–977 of SEQ ID NO:10 or a fragment comprising at least 10, at least 15, at least 20, at least 25, at least 40, or more than 40 consecutive bases of this nucleic acid. These nucleic acids may be used in the nucleic acid based detection procedures described above or to express polypeptides for use in diagnostic methods.

Polypeptides encoded by the ORFs, antigenic epitopes encoded by the ORFs, or fragments comprising at least 10, at least 15, or at least 25 consecutive amino acids thereof may be used to specifically identify infected animals or as compositions for inducing an immune response against *Haemobartonella felis*. Immunogenic polypeptides, antigenic epitopes therefrom, or fragments thereof which are specific for *Haemobartonella felis* may be identified as described in Example 6 below.

EXAMPLE 6

Identification of Polypeptides Specific for *Haemobartonella felis*

The ORFs described above (or nucleic acids comprising fragments of the ORFs which encode a prospective antigenic epitope) are cloned and inserted into an expression vector. The expression vector may be any of those familiar to those skilled in the art, including DNA, RNA and viral vectors. If desired, the ORFs or fragments thereof may be linked to nucleic acids encoding another polypeptide to express a chimeric fusion protein.

The expression vector is introduced into a suitable host cell for protein expression. The host cell may be a mammalian, bacterial, fungal, or insect cell.

To determine whether the ORFs or fragments thereof encode immunogenic polypeptides, the polypeptides expressed from the expression vector are purified using conventional techniques such as chromatography, gel electrophoresis, or affinity columns. The polypeptides are contacted with immune serum, plasma, or blood from animals infected with *Haemobartonella felis*. Binding of antibodies in the immune serum, plasma, or blood to the polypeptides encoded by the expression vectors is detected using a secondary antibody. To identify polypeptides which are specific for *Haemobartonella felis*, the polypeptides encoded by the expression vector are also contacted with immune serum, plasma, or blood from animals which are not infected with *Haemobartonella felis* or with antibodies directed against antigens from organisms related to *Haemobartonella felis*. Polypeptides which are bound by antibodies from animals infected with *Haemobartonella felis* but not antibodies from uninfected animals or antibodies against related organisms may be used to specifically identify animals infected with *Haemobartonella felis*.

Those polypeptides (or fragments thereof which contain an antigenic epitope) which are identified as being immunogenic using the above procedures may be used in immunological diagnostics to determine whether a mammal is infected with *H. felis*. These diagnostics may utilize any of the immunological assays familiar to those skilled in the art, including ELISA assays, radioimmunological assays, competition assays, sandwich assays, Western blots, and in situ antibody binding assays.

In such immunological diagnostics, a polypeptide having a sequence selected from the group consisting of SEQ ID Nos: 11–15 (or a fragment of these polypeptides containing an antigenic epitope) is contacted with a sample of a bodily fluid, such as blood, serum, plasma, saliva, or urine, from a mammal to be tested for infection with *H. felis*. Preferably, the polypeptide or fragment thereof which is utilized in the immunological diagnostic is a recombinant polypeptide obtained from expression vectors such as those described above.

Preferably the polypeptide or fragment thereof is attached to a solid support such as a microwell plate, a bead, or a chromatography strip.

The binding of antibodies in the bodily fluid to the polypeptide or fragment thereof is detected using any of the detection agents known to those of skill in the art, including secondary antibodies having a detectable enzymatic activity or a radioactive label thereon. Where the polypeptide or fragment thereof is attached to the support, the binding of antibodies in the binding of antibodies in the bodily fluid samples to the polypeptide or fragment is detected by detecting the presence of the antibodies from the bodily fluid on the solid support.

In a preferred embodiment, the immunological diagnostic uses an ELISA assay to detect infection with *H. felis*. Example 7 describes the use of the polypeptides encoded by the ORFs in ELISA assays. Example 7 below describes the use of the polypeptides of SEQ ID NOs: 11–15 in ELISA based assays.

EXAMPLE 7

Diagnosis of *Haemobartonella felis* Infection by ELISA Analysis

A nucleic acid encoding a polypeptide having a sequence selected from the group consisting of SEQ ID Nos: 11–15

(or a nucleic acid encoding an antigenic epitope within these polypeptides) is cloned into an expression vector and the encoded polypeptide is obtained from cultured cells containing the vector. Alternatively, the polypeptide or fragment thereof may be purified or enriched using biochemical techniques familiar to those skilled in the art. In another embodiment, immunogenic peptides from the polypeptides encoded by the ORFs may be synthesized in vitro.

The polypeptide or fragment thereof is coated at 50 μg/ml on the wells of microtiter plates using Carbonate coating buffer pH 9.6 overnight. The plates are washed with PBS/Tween 3x, and sera from the subjects to be tested for *Haemobartonella felis* infection is applied. Each sera is diluted in blocking buffer (PBS/Tween with 500 μg/ml MBP) and applied to the coated wells for 1 hour at 37° C. The plates are washed with PBS/Tween, and an anti-cat IgG biotin conjugated monoclonal antibody (Sigma) is added (1:1000) for 1 hour at room temp. After washing, Extravidin/Alkaline phosphatase conjugate (Sigma) at 1:1000 in PBS/Tween is added for 30 minutes at room temperature. After a final washing step, plates are developed with nitrophenylphosphate substrate (Sigma). As a control, the same steps are performed on microtiter wells which have not been coated with the polypeptides encoded by the ORFs or fragments thereof or wells which have been coated with a control polypeptide. A color level higher than that observed in the control wells indicates that the subject is infected with *Haemobartonella felis*.

The above procedures were performed using ORF4 (nucleotides 420–941 of SEQ ID NO: 10) to confirm that the polypeptide encoded by ORF4, which has the amino acid sequence of SEQ ID NO: 14, is immunogenic and is recognized by antibodies from animals infected with *Haemobartonella felis* but not by antibodies from uninfected animals. Example 8 describes the expression and preparation of the polypeptide of SEQ ID NO: 14.

EXAMPLE 8

Expression and Preparation of the Polypeptide of SEQ ID NO:14

To confirm that the polypeptide of SEQ ID NO:14, which is encoded ORF4, is expressed by *H. felis* and is immunogenic in the cat, ORF4 was inserted into an expression vector as follows. It should be noted that the fact that the polypeptide of SEQ ID NO:14 encoded by ORF4 does not commence with a codon for methionine does not preclude ORF4 from coding for an expressed protein, since others have found proteins from the related *M. gallisepticum* (see below) that commence with amino acids other than methionine. (See Markham, P. F., M. D. Glew, K. G. Whithear and I. D. Walker, Molecular Cloning of a Member of the Gene Family that Encodes pMGA, a Haemagglutinin of *Mycoplasma gallisepticum*, Infect Immun 1993 61(3) 903–909, the disclosure of which is incorporated herein by reference).

A PCR product containing ORF4 was gel purified and cloned into the pCR 2.1 vector according to the manufacturers recommendations. A sequence analysis performed by Retrogen Inc., (6861 Nancy Ridge Rd., Suite D, San Diego calif. 92121) confirmed that the ORF 4 nucleotide sequence had been successfully cloned. The cloned ORF4 was then inserted into the pMAL-c2 expression vector according to the manufacturers recommendations (New England Biolabs) and the resulting construct was transfected into *E coli*.

Culture fluids from the transfected cells were subjected to purification on an amylose column according to the manufacturers instructions (New England Biolabs). A polypeptide was eluted which on disc electrophoresis had the expected molecular weight of the polypeptide of SEQ ID NO: 14. The polypeptide encoded by ORF4 was designated I-A. The yield of recombinant I-A protein obtained using the above procedure was 2 mg/l.

As described in Example 9 below, the purified recombinant I-A protein was used in an ELISA to investigate whether it would be bound by antibodies in sera from cats known to be infected with *Haemobartonella felis* but not by antibodies in sera from uninfected cats.

EXAMPLE 9

ELISA Assays Using the I-A Protein

Microwell plates were coated with I-A protein at 10 μg/ml for 2 hr. at 37° C. Sera (2.5 μl) from cats which were positive for FIA based on cytological assays or contrl sera from SPF cats which were negative for FIA were preincubated with 30 μl of a 1 mg/ml solution of maltose binding protein (MBP), for 2 hr. at 37° C. The coated wells were washed free of unbound I-A and wells were incubated with the preincubated sera at 1:200 dilution for 15 min. at room temperature. After washing, the wells were incubated a for 15 min. with biotin labeled anti-cat IgG antibody at a dilution of 1:1000. After a further wash, the wells were incubated with Extravidin labeled alkaline phosphatase at a dilution of 1:1000. After washing, the wells were incubated with the enzyme substrate, pPNP, and the resultant optical densities were determined. The results are given in Table I.

TABLE I

I-A ELISA on Sera from SPF Cats and *H. felis* Infected Cats

| Sample | $OD_{405}$ | |
|---|---|---|
| | SPF cats - FIA negative | FIA Cytology Positive |
| 1 | 0.050 | 0.549 |
| 2 | 0.149 | 0.510 |
| 3 | 0.091 | 0.509 |
| 4 | 0.211 | 0.331 |
| 5 | 0.130 | 0.321 |
| 6 | 0.126 | 0.801 |
| 7 | 0.149 | 0.909 |
| 8 | 0.033 | 0.411 |
| MEAN | 0.117 | 0.543 |
| SD | 0.058 | 0.212 |

All of the cats which were FIA positive based on cytological assays had a significant antibody titer to the I-A protein (third column). In contrast, FIA negative cats did not have meaningful antibody titers to I-A (second column). The fact that the mean titer against I-A in the infected cats was more than four times greater than the mean for the non-infected cats ($O.D_{405}$ 0.543 v. $O.D_{405}$ 0.117) demonstrates that the I-A protein is immunogenic in cats.

The above results demonstrate that the polypeptide of SEQ ID NO: 14 may be used in immunological assays to determine whether a mammal is infected with *Haemobartonella felis*. In a particularly preferred embodiment, the polypeptide used in the assay comprises a polypeptide having the sequence of SEQ ID NO:14 or an antigenic epitope within the polypeptide of SEQ ID NO: 14.

Antibodies capable of binding to the polypeptides encoded by the ORFs may be obtained as described in Example 10 below.

EXAMPLE 10

Generation of Antibodies Against *Haemobartonella felis* Polypeptides

A. Monoclonal Antibodies

The polypeptides encoded by the ORFs described above (or fragments comprising an antigenic epitope in said polypeptides) are isolated from host cells containing expression vectors encoding the polypeptides or fragments thereof. Monoclonal antibody to epitopes in the polypeptides or fragments thereof can be prepared from murine hybridomas according to the classical method of Kohler, G. and Milstein, C., *Nature* 256:495 (1975) or derivative methods thereof. Briefly, a mouse is repetitively inoculated with a few micrograms of the selected polypeptide or fragment thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, N.Y. Section 21–2.

B. Polyclonal Antibody Production by Immunization

Polyclonal antiserum containing antibodies to heterogenous epitopes of a single polypeptide or fragment thereof can be prepared by immunizing suitable animals with a polypeptide encoded by the ORFs described above (or a fragment comprising an antigenic epitope in said polypeptides) which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: *Manual of Clinical Immunology,* 2d Ed. (Rose and Friedman, Eds.) Amer. Soc. For Microbiol., Washington, D.C. (1980).

The antibodies obtained using the procedures of Example 10 may be used to determine whether a subject is infected with *Haemobartonella felis* as follows. A tissue sample is obtained from the sample to be tested. The sample is contacted with antibodies specific for *Haemobartonella felis* and the ability of the antibodies to bind to the tissue sample is determined. Binding of the antibodies to the sample can be detected by labeling the antibody or by using a secondary antibody capable of binding to the antibody against the *Haemobartonella felis* polypeptide or peptide. If binding of the antibody to the sample is observed, the subject is infected with *Haemobartonella felis*.

The polypeptides of SEQ ID Nos: 11–15 encoded by the ORFs in the sequence of SEQ ID NO:10 (or fragments of these polypeptides comprising an antigenic epitope) may also be used to induce an immune response against *Haemobartonella felis* as described in Example 11. In a preferred embodiment, the polypeptide used to induce the immune response against *Haemobartonella felis* comprises a polypeptide having the sequence of SEQ ID NO: 14 or a fragment thereof comprising an antigenic epitope.

EXAMPLE 11

Use of the Polypeptides Encoded by the ORFs to Induce an Immune Response

A polypeptide having the amino acid sequence of one of SEQ ID Nos: 11–15 (or a fragment thereof comprising an antigenic epitope) is isolated from host cells containing an expression vector encoding the polypeptide or fragment thereof. If desired, a fusion protein between the antigenic polypeptide and another peptide may be used to induce an immune response. The polypeptide may be isolated using conventional techniques. Alternatively, immunogenic peptides may be synthesized in vitro.

The polypeptide, immunogenic fragment thereof, or fusion protein containing the polypeptide is mixed with a pharmaceutically acceptable carrier such as those typically employed in vaccines. If desired, a standard adjuvant may also be added to the mixture to enhance the immune response.

The mixture is administered to the subject, causing an immune response to be generated against an antigenic site or sites in the polypeptide, immunogenic fragment thereof, or fusion protein. Preferably, the immune response is sufficient to protect the subject from infection with *Haemobartonella felis*. If desired, the administration may be repeated several times to enhance the immune response.

Another aspect of the invention is a method for culturing *Haemobartonella felis*. Prior to the present invention, it was not possible to culture *Haemobartonella felis*. A procedure for culturing *Haemobartonella felis* is described in Example 12 below.

EXAMPLE 12

Method for Culturing *Haemobartonella felis*

A feline blood sample (HF035) from patient "Max Holyote" was obtained from STAT Veterinary testing laboratory (Rancho Santa Fe, Calif.) and was found to be positive for *Haemobartonella felis* by cytology and PCR using the procedures described above. A 1 ml sample of the blood was diluted into a mixture of 1 ml of SPF (Specific Pathogen Free) whole feline blood and 10 ml of TSB broth (Tryptic Soy Base, from Difco Laboratories, Detroit, Mich.) supplemented with ascorbic acid (1 $\mu$g per ml), and glutathione (4 $\mu$g per ml). The culture was incubated at 39° C. After 8 days of incubation, a sample was removed from the culture and found positive for *Haemobartonella felis* by PCR using the procedures described above. A month after incubation was initiated, a further sample was tested by PCR using the procedures described above and was found to be positive for *Haemobartonella felis*. In contrast, an aliquot of the original blood which had been maintained at 4° C. for the month, was now found to be negative for *Haemobartonella felis*. For the first time, conditions for maintaining *Haemobartonella felis* in culture have been achieved. This is evident from the finding that after a month in the medium, held at 39° C., the organism was still detectable, while when kept for the same period of time at 4° C. in the absence of the medium, the organism died.

The above culture conditions permit large amounts of the organism to be cultured. This facilitates the diagnosis of infection (or previous infection) by *Haemobartonella felis* by detecting antibodies to the organism in ELISA or other immunodiagnostic assays such as those described above.

In addition, following harvesting and killing by heat, chemicals or irradiation, or inactivation using techniques familiar to those skilled in the art, the cultured *Haemobartonella felis* may be used as a protective vaccine. In such procedures the killed or inactivated organism is administered to a subject in a carrier such as those typically employed in the vaccine art. Preferably, the killed or inactivated organism is administered at a dosage sufficient to induce a protective immune response. The killed or inactivated organism may be administered in a single dose or in multiple doses.

Alternatively, *Haemobartonella felis* may be cultured as described above and mutagenized using techniques familiar to those skilled in the art, such as chemical mutagenesis, UV-mediated mutagenesis, site directed mutagenesis, or random mutagenesis to create avirulent strains of *Haemobartonella felis* which may be used to induce an immune response as described above.

The cultured *Haemobartonella felis* may also be used to construct expression libraries capable of expressing the genes encoded by the *Haemobartonella felis* genome. Techniques for constructing expression libraries are familiar to those skilled in the art and are described in Sambrook et. al., supra.

Briefly, expression libraries may be constructed as follows. To construct a cDNA expression library, *Haemobartonella felis* is cultured as described above. The mRNAs expressed by the cultured *Haemobartonella felis* are isolated and a first strand of cDNA is constructed by extending a first primer, such as a polyT oligonucleotide or a random oligonucleotide, from the 3' end of the mRNA. Thereafter, the second cDNA strand is synthesized using the first cDNA strand as a template. The resulting double stranded cDNAs are cloned into an expression vector such that the cDNAs are operably linked to a promoter capable of directing their expression. A variety of expression vectors suitable for the construction of cDNA expression libraries are familiar to those skilled in the art. The resulting expression library is then introduced into a suitable host cell.

Alternatively, an expression library may be constructed from genomic DNA. In such procedures, *Haemobartonella felis* is cultured as described above. Genomic DNA is isolated from the cultured *Haemobartonella felis* and inserted into an expression vector. The resulting expression library is then introduced into a suitable host cell.

Immunogenic proteins expressed from the expression libraries may be identified by screening the expression libraries with antiserum from *Haemobartonella felis* infected cats and uninfected control cats. Clones which are bound by antiserum from *Haemobartonella felis* infected animals but not by antiserum from the control animals express an immunogenic protein. These clones are then sequenced and characterized. The proteins expressed from these clones may be used in the diagnostics and vaccines described above.

Another aspect of the present invention relates to the use of antigens expressed by Mycoplasma, and in particular the avian pathogen *Mycoplasma gallisepticum*, to determine whether a mammal is infected with *H. felis* or to induce an immune response against *H. felis* in a mammal. This aspect of the invention is based on the observation that *H. felis* and *Mycoplasma gallisepticum* are closely related.

In order to identify organisms related to *H. felis* which might encode antigens useful for determining whether a mammal is infected with *H. felis* or inducing an immune response against *H. felis* in a mammal, the sequence of the *H. felis* 23S rRNA obtained above was used to search the Entrez database for homologous sequences using the MacVector DNA alignment program. The highest homology was with several species of the intracellular parasites of the genus Mycoplasma. *Mycoplasma gallisepticum*, a well studied member of the genus, was selected for further investigation.

To confirm that antigens expressed by *Mycoplasma gallisepticum* are recognized by antibodies in the serum, plasma, or blood of cats infected with *H. felis* but not by antibodies in the serum, plasma, or blood of control cats which are not infected with *H. felis*, the experiments of Example 13 were conducted.

EXAMPLE 13

Demonstration that *Mycoplasma gallisepticum* Expresses Antigens Which are Recognized by Antibodies From Cats Infected With *H. felis* but not by Antibodies from Uninfected Cats An isolate of *Mycoplasma gallisepticum* was purchased from the American Type Culture Collection (Edward deposit [ATCC 19610]) and grown as provided. The culture was lysed with TN3 detergent buffer and used to coat microwell plates at a concentration of 60 µg/ml in carbonate buffer. After overnight incubation and subsequent washing, the coated plates were contacted with sera from 18 cats that were suspected of being FIA positive by cytology, 3 cats determined to be FIA positive by cytology and PCR, and 4 cats that were negative for FIA by PCR. Sera were diluted 1:200 in PBS and incubated for 15 min. in coated wells. After washing, the wells were then incubated for 15 min. with biotin labeled anti-cat IgG antibody at a dilution of 1:1000 After a further wash, the wells were incubated with Extravidin labeled alkaline phosphatase at a dilution of 1:1000. Following a further wash, the wells were incubated with the enzyme substrate, pPNP, and the resultant optical density determined. The results are given in Table II. (Note that cats 1–4 in Table II were SPF cats which were known to be free of *H. felis* infection).

TABLE II

A Comparison of FIA Diagnosis by *M. gallisepticum* ELISA, PCR and Cytology

| Cat No | PCR | Cytology | $OD_{405}$ |
|---|---|---|---|
| SECTION 1 | | | |
| 1 | neg. | neg. | 0.176 |
| 2 | neg. | neg. | 0.013 |
| 3 | neg. | neg. | 0.133 |
| 4 | neg. | neg. | 0.059 |
| MEAN | neg. | neg. | 0.093 |
| SD | | | 0.074 |
| SECTION 2 | | | |
| 5 | pos. | pos. | 1.028 |
| 6 | pos. | pos. | 1.154 |
| 7 | pos. | pos. | 1.041 |
| MEAN | pos. | pos. | 1.074 |
| SD | | | 0.069 |
| SECTION 3 | | | |
| 8 | ND | pos. | 1.168 |
| 9 | ND | pos. | 0.083 |
| 10 | ND | pos. | 1.293 |
| 11 | ND | pos. | 1.244 |
| 12 | ND | pos. | 1.201 |
| 13 | ND | pos. | 1.210 |
| 14 | ND | pos. | 1.210 |
| 15 | ND | pos. | 1.130 |
| 16 | ND | pos. | 0.348 |
| 17 | ND | pos. | 1.209 |
| 18 | ND | pos. | 1.240 |
| 19 | ND | pos. | 0.080 |
| 20 | ND | pos. | 0.530 |
| 21 | ND | pos. | 0.566 |
| 22 | ND | pos. | 1.180 |
| 23 | ND | pos. | 0.111 |
| 24 | pos. | pos. | 0.354 |
| 26 | pos. | pos. | 0.010 |
| MEAN | | | 0.787 |
| SD | | | 0.506 |

The results indicate that *H. felis* shares one or more strong immunogens with *M. gallisepticum,* since cats definitively known to be infected with *H. felis* (as determined by both cytology and PCR), have high levels of antibody against *M. gallisepticum* (Section 2). In addition, since cats that are not infected with *H. felis* (as determined both by cytology and PCR) do not have significant antibodies against *M. gallisepticum* (Section 1), the results indicate that *M. gallisepticum* antigens are useful for determining whether a mammal is infected with *H. felis* or for inducing an immune response against *H. felis* in a mammal.

Although the numbers of cats in sections 1 and 2 are low, the standard deviations of the mean titers are small. This indicates the signal to noise ratio in ELISA assays is low enough to allow their use in diagnostics for determining whether a mammal is infected with *H. felis.*

The high standard deviation in the cats of section 3 indicates that the group is heterogeneous and contains both infected and uninfected cats. This is most likely a result of the unreliability of cytological methods for detecting *H. felis* infection.

The above results indicate that one or more antigens expressed by Mycoplasma, and in particular *Mycoplasma gallisepticum*, are recognized by sera from cats infected with *H. felis* but not by sera from uninfected cats. Accordingly, these antigens, or portions thereof, may be used in immunological diagnostics to determine whether a mammal is infected with *H. felis*. The antigens used in such diagnostics may be obtained by conventional biochemical purification or enrichment techniques, in vitro peptide synthesis, or recombinant DNA based techniques.

In such diagnostics, a polypeptide expressed by Mycoplasma which has an epitope which is recognized by serum, plasma, or blood from mammals infected with *H. felis* but not by serum, plasma, or blood from uninfected mammals (or a fragment of the polypeptide which includes the epitope) is identified. The polypeptide may be the complete polypeptide expressed in Mycoplasma or, alternatively, the polypeptide may be a fragment of a polypeptide expressed in Mycoplasma which includes the epitope. In one embodiment, the polypeptide containing the epitope is a polypeptide expressed by *Mycoplasma gallisepticum.*

The immunological diagnostics may utilize any of the immunological assays familiar to those skilled in the art, including ELISA assays, radioimmunological assays, competition assays, sandwich assays, Western Blots, and in situ antibody binding assays. For the Western Blots and in situ antibody binding assays, antibodies against the Mycoplasma polypeptide may be produced as described in Example 10 above.

Preferably the polypeptide or fragment thereof is attached to a solid support such as a microwell plate, a bead, or a chromatography strip.

The binding of antibodies in bodily fluid samples, such as blood, serum, plasma, saliva, or urine to the polypeptide or fragment thereof is detected using any of the detection agents known to those of skill in the art, including secondary antibodies having a detectable enzymatic activity or a radioactive label thereon. Where the polypeptide or fragment thereof is attached to the support, the binding of antibodies in the bodily fluid samples to the polypeptide or fragment is detected by detecting the presence of the antibodies from the bodily fluid on the solid support.

Examples 14 and 15 describe the identification of a polypeptide expressed by *Mycoplasma gallisepticum* which is recognized by serum, plasma, or blood from mammals infected with *H. felis* but not by serum, plasma, or blood from uninfected mammals and the use of the identified polypeptide in ELISA assays to determine whether a mammal is infected with *H. felis.*

One candidate for the *Mycoplasma gallisepticum* antigen which was recognized by serum, plasma, or blood from mammals infected with *H. felis,* but not by serum, plasma, or blood from uninfected mammals is a hemagglutinin designated pMGA. The genome of a single strain of *Mycoplasma gallisepticum* contains a large repertoire of genes encoding related pMGA polypeptides. (See N. Basseggio et al., *Microbiology* 1996 142:1429–1435 Size and Genomic Location of the pMGA Multigene Family of *Mycoplasma gallisepticum*; P. F. Markham et al., *Infection and Immunity* 1992 60: 3885–3891, Characterization of a Major Hemagglutinin Protein from *Mycoplasma gallisepticum;* P. F. Markham et al., *Infection and Immunity* 1993 61: 903–909, Molecular Cloning of a Member of the Gene Family that Encodes pMGA, a Hemagglutinin of *Mycoplasma gallisepticum*; P. F. Markham et al., *FEBS Letters* 1994 352:347–352, The Organisation of the Multigene Family which Encodes the Major Cell Surface Protein, pMGA, of *Mycoplasma gallisepticum;* and Glew et al., *Microbiology* 1995 141:3005–3014, Expression Studies on Four Members of the pMGA Multigene Family in Size and Genomic Location of the pMGA Multigene Family of *Mycoplasma gallisepticum* S6, the disclosures of which are incorporated herein by reference). However, each strain generally expresses a single pMGA protein on its cell surface at a given time. The pMGA protein is expressed at a high level and is known to be highly immunogenic. As used herein, the terms "pMGA" encompasses all of the polypeptides encoded by this multigene family.

Example 14 below describes the production of recombinant *M. gallisepticum* pMGA protein.

EXAMPLE 14

Molecular Cloning and Recombinant Expression of the pMGA Protein of *M. gallisepticum* and its Use for the Diagnosis of FIA Using the isolate of *Mycoplasma gallisepticum* that was purchased from the American Type Culture Collection (Edward deposit [ATCC 19610]), the pMGA 1.1 gene was PCR amplified using Primer sets Myco 5/6 (Markham, P. F et al, (1993), supra). The PCR product was gel purified and cloned into the pCR 2.1 vector according to the manufacturers recommendations (Invitrogen). Sequence analysis was then performed by Retrogen Inc., (6861 Nancy Ridge Rd., Suite D, San Diego Calif. 92121). This sequence analysis confirmed that the desired pMGA 1.1 gene had been successfully cloned. The cloned *Mycoplasma gallisepticum* pMGA 1.1 gene was then inserted into the pMAL-c2 expression vector according to the manufacturers recommendations (New England Biolabs). The resulting construct was used to produce the pMGA 1.1 protein in *E. coli*. Purification of the protein from the culture medium was performed using an amylose column according to the manufacturers instructions (New England Biolabs).

To determine whether the purified recombinant pMGA 1.1 protein produced above was recognized by antibodies from mammals infected with *H. felis* but not by antibodies from uninfected mammals, an ELISA analysis was performed as described in Example 15 below.

EXAMPLE 15

ELISA Analysis With DMGA

Microwell plates were coated with the recombinant pMGA 1.1 produced above at 10 µg/ml for 2 hr. at 37° C. Test sera (2.5 µl) were preincubated with 30 µl of a 1 mg/ml solution of MBP for 2 hr. at 37° C. The coated wells were washed free of unbound pMGA 1.1 and wells were incubated with preincubated sera at 1:200 dilution for 15 min. at room temperature. After washing, the wells were then incubated for 15 min. with biotin labeled anti-cat IgG antibody at a dilution of 1:1000. After a further wash, the wells were incubated with Extravidin labeled alkaline phosphatase, at a 10 dilution of 1:1000. Following a further wash, the wells were incubated with the enzyme substrate, pPNP, and the resultant optical density determined. The results are given in Table III.

TABLE III

A Comparison of FIA Diagnosis by pMGA-ELISA, PCR and Cytology

| Serum | PCR | Cytology | $OD_{405}$ |
|---|---|---|---|
| SECTION 1 | | | |
| 3684-1 | neg. | neg. | 0.080 |
| 9/918 | neg. | neg. | 0.120 |
| 9/9-9 | neg. | neg. | 0.140 |
| 9/9-16 | neg. | neg. | 0.150 |
| 4921 | ? | neg. | 0.140 |

TABLE III-continued

A Comparison of FIA Diagnosis by pMGA-ELISA, PCR and Cytology

| Serum | PCR | Cytology | $OD_{405}$ |
|---|---|---|---|
| MEAN | | | 0.126 |
| SD | | | 0.028 |
| SECTION 2 | | | |
| 922 | pos. | pos. | 0.380 |
| 923 | pos. | pos. | 0.410 |
| 10--7 | pos. | pos. | 0.67 |
| SD | | | 0.477 |

The results shown in Table III demonstrate that pMGA 1.1 was recognized by antibodies from mammals infected with *H. felis* but not by antibodies from uninfected mammals. Although the number of samples is small, the fact that the mean OD for the infected group is at least five times greater than the mean for the uninfected group demonstrate that recombinant pMGA from *Mycoplasma gallisepticum* may be used in immunological assays, including ELISA assays, for determining whether a mammal is infected with *H. felis*.

Polypeptides expressed by Mycoplasma or fragments thereof which contain epitopes recognized by serum, plasma, or blood from mammals infected with *H. felis* but not by uninfected mammals may also be used to induce an immune response against *H. felis* in a mammal using the procedures provided in Example 11 above. The polypeptides used to induce the immune response may be administered in preparations enriched for the polypeptide by conventional biochemical enrichment procedures. Alternatively, the polypeptides may be synthesized in vitro. In another embodiment, the polypeptides may be recombinant polypeptides produced through genetic engineering.

In another embodiment, an immune response against *H. felis* may be induced by administering a killed, inactivated, or avirulent preparation of Mycoplasma, and in particular *Mycoplasma gallisepticum*, to the mammal. The killed, inactivated, or avirulent organism may be administered in a single dose or in multiple doses.

The methods described above facilitate the diagnosis of mammals infected with *Haemobartonella felis* using probes or primers derived from the *Haemobartonella felis* 16S and/or 23S ribosomal RNA genes. The invention also includes the nucleic acids used in such diagnostics, vectors containing these nucleic acids, and host cells containing the vectors. Using these techniques and reagents, the diagnosis of *Haemobartonella felis* infection can be performed rapidly, specifically, and with high sensitivity.

In addition, a *Haemobartonella felis* derived nucleic acid containing multiple open reading frames has been identified. This nucleic acid can be cloned into expression vectors and expressed in suitable host cells. The expressed proteins can be used for diagnostics and vaccines.

In addition, a method of culturing *Haemobartonella felis* is described. The cultured *Haemobartonella felis* may be used for vaccines or to construct expression libraries. The proteins expressed from the expression libraries can be used in diagnostics or vaccines.

Another aspect of the present invention is the use of polypeptides from Mycoplasma, and in particular *Mycoplasma gallisepticum*, in diagnostics for determining whether a mammal is infected with *Haemobartonella felis* or to induce an immune response against *Haemobartonella felis*.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All references and patent applications referred to herein are incorporated herein by reference in their entirety.

SEQUENCE LISTING

<160> NUMBER OF SEQ ID NOS: 15

<210> SEQ ID NO 1
<211> LENGTH: 18
<212> TYPE: DNA
<213> ORGANISM: Haemobartonella Felis

<400> SEQUENCE: 1
gacttggtgg ttatggcg                                              18

<210> SEQ ID NO 2
<211> LENGTH: 20
<212> TYPE: DNA
<213> ORGANISM: Artificial Sequence
<220> FEATURE:
<223> OTHER INFORMATION: Artificial Primer

<400> SEQUENCE: 2
catgaggact tgacgtcatc                                            20

<210> SEQ ID NO 3
<211> LENGTH: 3552
<212> TYPE: DNA
<213> ORGANISM: Haemobartonella Felis
<220> FEATURE:
<221> NAME/KEY: misc_feature
<222> LOCATION: (1)...(3552)
<223> OTHER INFORMATION: n = A, T, C or G

<400> SEQUENCE: 3
aagcttcatc catgatttag cttttaaagc cttcgggcgc tgagggattg ggatatgctc      60
tattagctag ttggcgggat aaaagcccac caaggcaatg atagattgct ggtcttagag     120
gatgaacagc cacaatggga ttgagatacg gcccatattc ntacgggaag cagcagtagg     180
gaatcttcca caatggacga aagtctgatg gagcaatacc atgtgaacga tgaaggcctt     240
tttggttgta aagttctttt acgagggata attatgatag tacttcgtga ataagtgaca     300
gcaaactatg tgccagcagc tgcggtaata cataggtcgc gagcattatt cggatttatt     360
gggcgtaaag caagcgcagg cggatgtgta agttctgtgt taaatgcagc tactcaatag     420
ttgtatgcac cgaatactac atgtctagat tgtggtaggg agtttcggaa ttaagcatgg     480
agcggtggaa tgtgtagata tgcttaagaa caccagaggc gccggcggaa acttaggcca     540
taaatgacgc ttaggcttga aagtgtgrgg agcaaatggg attagrtacc ccagtagtyc     600
acaccgtaaa cgatgggtat tagatattag ggctktagct ttagtgttgt agcttacgcg     660
ttaaataccc cgcctgggta gtacatatgc aaatatgaaa ctcaaaggaa ttgacgggga     720
cctgaacaag tggtggagca tgttgcttaa ttcgataata cacgaaaaac cttaccaagg     780
tttgacatcc ctcgcaaagc tatagaaata tagtagaggt tatcgaggtg acaggtggtg     840
catggctgtc gtcagctcgt gtcttgagat gtttggttaa gtcccgcaac gagcgcaacc     900
ccactcttta gttacttgtc taaagagrct gcacagtaat gtagaggaag gatgggatca     960
cgtcaagtca tcatgcccct tatgccttgg gctgcaaacg tgctacaatg gcgaacacaa    1020
tgtgttgcag accagcgatg gtaagctaat caccaaattt cgtctcagtt cggataggag    1080

```
gctgcaattc gcctccttga agttccaatc actagtaatc ccgtgtcagc tatatcgggg    1140
tgaatccgtt cccaggtctt gtacacaccg cccgtcaaac tatgagacca gtgggcattt    1200
aaaaatacat tcatttgtat ctagagtgaa cattctgatt ggagttaagt cgtaacaagg    1260
tacccgtacg agaacgtgcg ggtggataat cttcaagtta tgagatgata gagcctttt    1320 gggctttatt tagtagaggt tgtaactaga ataaattcaa gtcgtataga tagatttgaa    1380
aacttctagg cggatgattc tcagttttga gaaagctaga actttctcag tttgcttttg    1440
aaaggaaaag ataataaccg agttaactta gatngttnat catacgtaaa ttattaagag    1500
ctaaaggtgg atttcttgga aatggtagac tatgaaggac gtgccaatct gcgataagct    1560
aggggtagcc gatnagggc tttaatccct agatctccga atgtagaaat acaacatttt     1620
gaaagatttg ttacttgtcg gccaattcat aaccgacaag ggtgaacttc gtgaagtgaa    1680
acatctcagt ngcgaaagga aagaaagag aattcgattc cctcagtagt ggtgagcgaa     1740 agggaacag gccaaaccgg ttttaccggg gttgtaggac atttatatgg aatcagaagt     1800
ataggagaag tctttggaaa gagacggcat agagggcgat cccccgtat ccgacatgct     1860 tctgattact gagtgcatcc tgagtagggc gggacacgtg taatcctgtc tgaatctgcc    1920
cagaccattg ggtaagccta aatactaacc atttaccgat agtgaacaag tactgtgaag    1980
gaaagatgaa aagaacccag agatgggagt gaaatagatc atgaaaccta gcttacga     2040 agagtcatag gccatttatg gctaatggcg tgcgttttga agtatgagcc ggcgagttat    2100
tgttgcatgc aaggttaagc aatcaaaagc ggagccgtat cgaaagcgag tgtgaatagt    2160
gcgtttagta tgtggcaata gacccgaaac gggatgatct atccatgggc aggttgaagg    2220
tggagtaata tccattggag gaccgaaccg actaccgttg aaatgttagc ggatgacttg    2280
tggatagggg tgaaattcca atcgaattcc gtgatagctg gttctcgtcg aaatagtttt    2340
aggactagcg ttggattatc cgatgctttg gaggtaaagc actgaattca tgatggcgca    2400
atctttgtgt actgaatgaa attaaacttt gaatgccaaa gtgtctactc cagcagtgag    2460
actatggggg ataagctcca tggtcatgag ggaaagagcc cagactaaca aataaggtcc    2520
ctaaatttgg ctaagtggag aaggaagtcg aaattcttaa acaactagta tgttggctta    2580
gaagcagcca ccatttaaag agtgcgtaac agctcactag tctagttttt cggcaccgaa    2640
ggtataacgg ggctaagcca aataccgaat ttttagacta tttatatagt ggtagacgag    2700
tgttgtatta gcgcgaaggc tgagcgtgag cacagttgga gttaatacaa gtaaggatgc    2760
cggcgtgagt aacgtatgaa agttaaaatc tttctagccg attgatcaag gtttccaggg    2820
caagggtcat cctccctggg ttagtcggtc ctaagatgag gccgagaggc gtagtcgatg    2880
ggcagcgagt taatattctt gcaccagttt agctagtgat gggttgacag aagaggttaa    2940
tgcgggcggg ttactggatt cccgcttaag ctgcaagtgt ttngggtagt aaaatacgcc    3000
cgatttaagc gtgagcagtg aatacgagcg aaccctttcgg gtagtagtga agtcgcaaac    3060
atcatattct caagaaaaga ctctaaactt atggctaatc tgtccgtacc tagaacgaac    3120
acangtgatc agggagaata tcccaaggct atcgagataa ctatagttaa ggaactctgc    3180
aaaatagccc cgtaacttcg ggagaagggt gcctaatttg cnttaggcca cagtaaagaa    3240
tgagggggga ctgtttaaca aaaacatagc tttatgcgaa atcgtaagan naggtatatg    3300
aggnganacc tgcccagtgc cagaaggtca atgaaggatg ttagcttttg cgaagcattt    3360
aacttaagcc ctggtgaacg gcggccgtaa ctataacggt cctaaggtag cgaaattcct    3420
```

```
tgtcaggtaa attctgtccc gcttgaatgg tgtaaccatn tcttaactgt nttgacnata      3480
ggctcggtga atcctggtg agagtgaaga cactctcttg ccgctatggg acggaaagac      3540
cctatgaagc tt                                                          3552

<210> SEQ ID NO 4
<211> LENGTH: 24
<212> TYPE: DNA
<213> ORGANISM: Haemobartonella Felis

<400> SEQUENCE: 4
ctctttagac aagtaactaa agag                                              24

<210> SEQ ID NO 5
<211> LENGTH: 20
<212> TYPE: DNA
<213> ORGANISM: Haemobartonella Felis

<400> SEQUENCE: 5
caaatgggat tagrtacccc                                                   20

<210> SEQ ID NO 6
<211> LENGTH: 20
<212> TYPE: DNA
<213> ORGANISM: Haemobartonella Felis

<400> SEQUENCE: 6
gtcacctcga taacctctac                                                   20

<210> SEQ ID NO 7
<211> LENGTH: 21
<212> TYPE: DNA
<213> ORGANISM: Haemobartonella Felis

<400> SEQUENCE: 7
ctttagtgtt gtagcttacg c                                                 21

<210> SEQ ID NO 8
<211> LENGTH: 18
<212> TYPE: DNA
<213> ORGANISM: Haemobartonella Felis

<400> SEQUENCE: 8
ccatcgacta cgcctctc                                                     18

<210> SEQ ID NO 9
<211> LENGTH: 20
<212> TYPE: DNA
<213> ORGANISM: Haemobartonella Felis

<400> SEQUENCE: 9
tttatggcta atggcgtgcg                                                   20

<210> SEQ ID NO 10
<211> LENGTH: 977
<212> TYPE: DNA
<213> ORGANISM: Haemobartonella Felis
<220> FEATURE:
<221> NAME/KEY: CDS
<222> LOCATION: (3)...(80)
<221> NAME/KEY: CDS
<222> LOCATION: (81)...(365)
<221> NAME/KEY: CDS
<222> LOCATION: (366)...(419)
<221> NAME/KEY: CDS
```

```
<222> LOCATION: (420)...(944)
<221> NAME/KEY: CDS
<222> LOCATION: (945)...(977)
<221> NAME/KEY: misc_feature
<222> LOCATION: 186, 816, 860, 885, 952, 959
<223> OTHER INFORMATION: n = A, T, C or G

<400> SEQUENCE: 10 tt gat att gtg atg gga gaa tat cag aat att caa gat agt aac cca        47
   Asp Ile Val Met Gly Glu Tyr Gln Asn Ile Gln Asp Ser Asn Pro
     1               5                  10                  15 gta ttc ttc ttc cca gca cta tcc caa tat tga cta ctt aaa aga agc       95
Val Phe Phe Phe Pro Ala Leu Ser Gln Tyr     Leu Leu Lys Arg Ser
             20                  25                          30 cta att cag cag tat gaa aag gtt ttg aat atc tat tta ata gat gac      143
Leu Ile Gln Gln Tyr Glu Lys Val Leu Asn Ile Tyr Leu Ile Asp Asp
             35                  40                  45 aac tac gac ata ttt gaa gat gag att aga caa gct aag gta ntt aga      191
Asn Tyr Asp Ile Phe Glu Asp Glu Ile Arg Gln Ala Lys Val Xaa Arg
         50                  55                  60 aat aaa gac tct ttg aat aat tta atc tgg aag ctt cag aaa ata gat      239
Asn Lys Asp Ser Leu Asn Asn Leu Ile Trp Lys Leu Gln Lys Ile Asp
     65                  70                  75 cct gaa ttt aat gag tca tac aag cag tca cag aag aat ctt ctc ttc      287
Pro Glu Phe Asn Glu Ser Tyr Lys Gln Ser Gln Lys Asn Leu Leu Phe
 80                  85                  90 cta aag gat atg aag gga agt gtg gaa cct gga ggt ggt tct gag att      335
Leu Lys Asp Met Lys Gly Ser Val Glu Pro Gly Gly Gly Ser Glu Ile
 95                 100                 105                 110 cca gat gat tta ggg gaa ctg gag tgt tga gga agg att gaa aaa ctt      383
Pro Asp Asp Leu Gly Glu Leu Glu Cys     Gly Arg Ile Glu Lys Leu
                115                 120                 125 gga aca gtt tat tac aga aca aga cgc ttt cct taa gaa gtg aga gcc      431
Gly Thr Val Tyr Tyr Arg Thr Arg Arg Phe Pro     Glu Val Arg Ala
                130                 135                 140 gga aat aat aag atc agg aac ttg gag aaa ttt gag ctc tac aca gat      479
Gly Asn Asn Lys Ile Arg Asn Leu Glu Lys Phe Glu Leu Tyr Thr Asp
            145                 150                 155 gcc aag ttg act cag aag tac ata aga ctt atg gga gtt caa att aga      527
Ala Lys Leu Thr Gln Lys Tyr Ile Arg Leu Met Gly Val Gln Ile Arg
            160                 165                 170 cat gat gac agt aag aac ctt ttg aga tta act aag tcc ctt cat gat      575
His Asp Asp Ser Lys Asn Leu Leu Arg Leu Thr Lys Ser Leu His Asp
            175                 180                 185 gct tgg act tcc cta ttt gag aag ata agt gaa gag gat gaa gct att      623
Ala Trp Thr Ser Leu Phe Glu Lys Ile Ser Glu Glu Asp Glu Ala Ile
        190                 195                 200 aag cat cag ttt atg aag tct gaa aag tcc tat gtt aag aat tac tac      671
Lys His Gln Phe Met Lys Ser Glu Lys Ser Tyr Val Lys Asn Tyr Tyr
205                 210                 215                 220 aag ctc tta gtt aga aag tac ttc aaa ttt gaa tcc aac cgt caa ttt      719
Lys Leu Leu Val Arg Lys Tyr Phe Lys Phe Glu Ser Asn Arg Gln Phe
                225                 230                 235 gat gaa ctt tca gct tcg gat gct ggc tta ata att agt cgc tct ttc      767
Asp Glu Leu Ser Ala Ser Asp Ala Gly Leu Ile Ile Ser Arg Ser Phe
                240                 245                 250 gat tat tta aaa gag cgt gac caa ctt atg gag aag gcg aag gag gcc      815
Asp Tyr Leu Lys Glu Arg Asp Gln Leu Met Glu Lys Ala Lys Glu Ala
            255                 260                 265 ngt gtt gaa gag aag tgg aag att gct tat aga tta tgg gag ttn aat      863
Xaa Val Glu Glu Lys Trp Lys Ile Ala Tyr Arg Leu Trp Glu Xaa Asn
```

```
                    270                 275                 280
gag ata agg aag aac ata tgc nag gcc tac ttg gat ata gat tcc gat         911
Glu Ile Arg Lys Asn Ile Cys Xaa Ala Tyr Leu Asp Ile Asp Ser Asp
285                 290                 295                 300 ttc tct aag tgg gtt gcc cgc tat gaa agc taa cta ctt anc tgg tcn         959
Phe Ser Lys Trp Val Ala Arg Tyr Glu Ser     Leu Leu Xaa Trp Xaa
                305                 310                     315 atc agg gtt gga att agt                                                 977
Ile Arg Val Gly Ile Ser
                320
```

<210> SEQ ID NO 11
<211> LENGTH: 25
<212> TYPE: PRT
<213> ORGANISM: Haemobartonella Felis

<400> SEQUENCE: 11

```
Asp Ile Val Met Gly Glu Tyr Gln Asn Ile Gln Asp Ser Asn Pro Val
1               5                   10                  15

Phe Phe Phe Pro Ala Leu Ser Gln Tyr
            20                  25
```

<210> SEQ ID NO 12
<211> LENGTH: 94
<212> TYPE: PRT
<213> ORGANISM: Haemobartonella Felis
<220> FEATURE:
<221> NAME/KEY: VARIANT
<222> LOCATION: 36
<223> OTHER INFORMATION: Xaa = Any Amino Acid

<400> SEQUENCE: 12

```
Leu Leu Lys Arg Ser Leu Ile Gln Gln Tyr Glu Lys Val Leu Asn Ile
1               5                   10                  15

Tyr Leu Ile Asp Asp Asn Tyr Asp Ile Phe Glu Asp Glu Ile Arg Gln
            20                  25                  30

Ala Lys Val Xaa Arg Asn Lys Asp Ser Leu Asn Asn Leu Ile Trp Lys
            35                  40                  45

Leu Gln Lys Ile Asp Pro Glu Phe Asn Glu Ser Tyr Lys Gln Ser Gln
        50                  55                  60

Lys Asn Leu Leu Phe Leu Lys Asp Met Lys Gly Ser Val Glu Pro Gly
65                  70                  75                  80

Gly Gly Ser Glu Ile Pro Asp Asp Leu Gly Glu Leu Glu Cys
                85                  90
```

<210> SEQ ID NO 13
<211> LENGTH: 17
<212> TYPE: PRT
<213> ORGANISM: Haemobartonella Felis

<400> SEQUENCE: 13

```
Gly Arg Ile Glu Lys Leu Gly Thr Val Tyr Tyr Arg Thr Arg Arg Phe
1               5                   10                  15

Pro
```

<210> SEQ ID NO 14
<211> LENGTH: 174
<212> TYPE: PRT
<213> ORGANISM: Haemobartonella Felis
<220> FEATURE:
<221> NAME/KEY: VARIANT
<222> LOCATION: 133, 147, 156

```
<223> OTHER INFORMATION: Xaa = Any Amino Acid

<400> SEQUENCE: 14

Glu Val Arg Ala Gly Asn Asn Lys Ile Arg Asn Leu Glu Lys Phe Glu
1               5                   10                  15

Leu Tyr Thr Asp Ala Lys Leu Thr Gln Lys Tyr Ile Arg Leu Met Gly
            20                  25                  30

Val Gln Ile Arg His Asp Asp Ser Lys Asn Leu Leu Arg Leu Thr Lys
        35                  40                  45

Ser Leu His Asp Ala Trp Thr Ser Leu Phe Glu Lys Ile Ser Glu Glu
    50                  55                  60

Asp Glu Ala Ile Lys His Gln Phe Met Lys Ser Glu Lys Ser Tyr Val
65                  70                  75                  80

Lys Asn Tyr Tyr Lys Leu Leu Val Arg Lys Tyr Phe Lys Phe Glu Ser
                85                  90                  95

Asn Arg Gln Phe Asp Glu Leu Ser Ala Ser Asp Ala Gly Leu Ile Ile
            100                 105                 110

Ser Arg Ser Phe Asp Tyr Leu Lys Glu Arg Asp Gln Leu Met Glu Lys
        115                 120                 125

Ala Lys Glu Ala Xaa Val Glu Glu Lys Trp Lys Ile Ala Tyr Arg Leu
    130                 135                 140

Trp Glu Xaa Asn Glu Ile Arg Lys Asn Ile Cys Xaa Ala Tyr Leu Asp
145                 150                 155                 160

Ile Asp Ser Asp Phe Ser Lys Trp Val Ala Arg Tyr Glu Ser
                165                 170

<210> SEQ ID NO 15
<211> LENGTH: 11
<212> TYPE: PRT
<213> ORGANISM: Haemobartonella Felis
<220> FEATURE:
<221> NAME/KEY: VARIANT
<222> LOCATION: 3, 5
<223> OTHER INFORMATION: Xaa = Any Amino Acid

<400> SEQUENCE: 15

Leu Leu Xaa Trp Xaa Ile Arg Val Gly Ile Ser
1               5                   10
```

What is claimed is:

1. A method for detecting the presence of *Haemobartonella felis* in a mammal comprising the steps of:
   obtaining a sample of a bodily fluid from said mammal;
   contacting said sample with an antigen from Mycoplasma, said antigen from Mycoplasma being an antigen which is recognized by antibodies in serum, plasma, or blood from mammals infected with *Haemobartonella felis* but not by antibodies in serum, plasma, or blood from mammals which are not infected with *Haemobartonella felis*; and
   determining whether said antibodies in said sample bind to said antigen from Mycoplasma.

2. The method of claim 1, wherein said antigen from Mycoplasma comprises the pMGA protein of *Mycoplasma gallisepticum* or a fragment thereof containing an antigenic epitope.

3. The method of claim 2, wherein said antigen comprises the pMGA 1.1 protein of the strain of *Mycoplasma gallisepticum* having the ATCC deposit number 19610 or a fragment thereof containing an antigenic epitope.

4. A method for detecting the presence of *Haemobartonella felis* in a mammal comprising the steps of:
   growing a culture of Mycoplasma cells, said Mycoplasma cells expressing an antigen which is recognized by antibodies in serum, plasma, or blood from mammals infected with *Haemobartonella felis* but not by antibodies in serum, plasma, or blood from mammals which are not infected with *Haemobartonella felis*;
   fixing said antigen to a solid support;
   contacting said solid support with a sample of a bodily fluid from said mammals; and
   determining whether antibodies in said sample bind to said antigen from Mycoplasma.

5. The method of claim 4, wherein said culture comprises a culture of *Mycoplasma gallisepticum*.

* * * * *